(12) United States Patent
Giaccia et al.

(10) Patent No.: US 7,378,246 B2
(45) Date of Patent: May 27, 2008

(54) METHODS AND COMPOSITIONS FOR REGULATING ADIPOGENESIS

(75) Inventors: Amato J. Giaccia, Stanford, CA (US); Zhong Yun, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 167 days.

(21) Appl. No.: 10/524,919

(22) PCT Filed: Feb. 28, 2003

(86) PCT No.: PCT/US03/06360

§ 371 (c)(1), (2), (4) Date: Feb. 17, 2005

(87) PCT Pub. No.: WO03/072064

PCT Pub. Date: Sep. 4, 2003

(65) Prior Publication Data

US 2005/0282167 A1   Dec. 22, 2005

Related U.S. Application Data

(60) Provisional application No. 60/360,689, filed on Feb. 28, 2002.

(51) Int. Cl.
*G01N 33/53* (2006.01)

(52) U.S. Cl. .................................................. 435/7.1

(58) Field of Classification Search ...................... None
See application file for complete search history.

(56) References Cited

OTHER PUBLICATIONS

Yun et al., Inhibition of PPAR gamma 2 gene expression by the HIF-1-regulated gene DEC1/Stra13: a mechanism for regulation of adipogenesis by hypoxia, Dev. Cell, Mar. 2002 vol. 2, No. 3, pp. 331-341.*

* cited by examiner

*Primary Examiner*—Robert B. Mondesi
(74) *Attorney, Agent, or Firm*—William E. Beaumont; Dickinson Wright, PLLC

(57) ABSTRACT

According to the disclosure hypoxia-mediated adipogenic inhibition involves the repression of PPARγ2 expression and its activity is a common mechanism for adipogenic inhibition by a variety of stimuli. The present disclosure relates to methods and compositions for regulating adipogenesis. The disclosure provides compositions comprising one or more DEC1/Stra13 fragments of capable of inhibiting PPARγ2 promoter activity. These fragments, e.g. the basic helix loop helix domain or amino acids 1-141, have substantially the same PPARγ2 promoter repressing activity as the full length polypeptide. The present disclosure provides methods of inhibiting adipogenesis comprising contacting a cell with a fragment of DEC1/Stra13. The invention further relates to methods and compositions of inhibiting angiogenesis in a tumor comprising contacting a tumor or tumor cell with a DEC1/Stra13 agonist.

11 Claims, 7 Drawing Sheets
(1 of 7 Drawing Sheet(s) Filed in Color)

A

B

C

A

B

C

A

Control HA-DEC1

DEC1 N1

B

C

TAT-N1 (DEC1 aa1-141), μM 0    0.2    1    5

METHODS AND COMPOSITIONS FOR REGULATING ADIPOGENESIS

BACKGROUND OF THE INVENTION

This application claims the benefit of U.S. Provisional Application No. 60/360,689 filed Feb. 28, 2002.

This invention was made with government support under National Institutes of Health Grants CA88480 and CA67166 and under National Institutes of Health Cancer Biology Training Grant CA09302. The government has certain rights in the invention.

Molecular oxygen ($O_2$) is vital to nearly all forms of lives on earth perhaps via its role in energy homeostasis, embryogenesis and differentiation. In response to hypoxia or low $O_2$ tensions, mammals increase the expression of a wide variety of genes including erythropoietin, vascular endothelial growth factor (VEGF) and glycolytic enzymes to stimulate erythropoiesis, angiogenesis, and glycolysis (Bunn and Poyton, 1996). Most of these hypoxia-regulated genes are transcriptionally induced by the hypoxia-inducible factor-1 (HIF-1), a member of the basic helix-loop-helix Per, AhR and Sim (bHLH-PAS) family (Semenza and Wang, 1992; Wang et al., 1995a). Under normoxia, HIF-1α protein becomes hydroxylated at proline-564 in its $O_2$-dependent degradation domain (Ivan et al., 2001; Jaakkola et al., 2001), and is targeted by the von Hippel-Lindau (VHL) protein for proteosome-mediated degradation (Maxwell et al., 1999; Ohh et al., 2000). Under hypoxia, HIF-1α becomes stabilized, translocates to the nucleus, and dimerizes with the $O_2$-independent HIF-1β to initiate gene expression (Jewell et al., 2001; Kallio et al., 1997). The importance of cellular responses to hypoxia in development and differentiation is demonstrated in mouse models in which homozygous deletion of either HIF-1α or HIF-1β is embryonically lethal. The HIF-1α$^{-/-}$ embryos succumb between 9 and 10 days post coitus (d.p.c) to loss of mesenchymal cells and impaired vascular development (Iyer et al., 1998; Ryan et al., 1998). The HIF-1$^{-/-}$ embryos die by 10.5 d.p.c due to vascular deficiencies in the yolk sac and/or placenta (Kozak et al., 1997; Maltepe et al., 1997). Interestingly, mice heterozygous for HIF-1α exhibit increased weight loss when subjected to chronic hypoxia (Yu et al., 1999), reinforcing the essential and complex role HIF-1α plays in cellular homeostasis in a low $O_2$ environment.

During the first trimester, a human embryo is located in a low $O_2$ environment (3% $O_2$) (Rodesch et al., 1992). In rat embryos, $O_2$ tensions are low before 9.5 d.p.c (Mitchell and Yochim, 1968). The establishment of uteroplacental circulation relies on cytotrophoblast invasion into the uterine spiral arterioles. Studies indicate that cytotrophoblasts proliferate with a poorly differentiated phenotype at low $O_2$ tensions and differentiate into a highly invasive phenotype at high $O_2$ tensions (Caniggia et al., 2000; Genbacev et al., 1997). High $O_2$ tensions also favor terminal differentiation of megakaryocytes into platelets (Mostafa et al., 2000). In contrast, differentiation of other cell types seems to prevail at lower $O_2$ tensions. At 3% $O_2$, rat mesencephalic precursor cells exhibit higher growth rates and higher levels of differentiation into a dopaminergic phenotype than at 20% $O_2$ (Studer et al., 2000). Low $O_2$ tensions have been found to promote osteochondrogenesis. Mesenchymal stem cells from rat bone marrow display enhanced colony-forming capability and increased proliferation at 5% $O_2$ as compared to 20% $O_2$, and they produce more osteocytes when implanted in vivo (Lennon et al., 2001). These observations suggest that the effect of $O_2$ on cell differentiation is extensive and cell-type specific.

Peripheral evidence in the literature supports a role of HIF-1 in adipogenesis. Using a subtraction cloning approach, Imagawa et al. (1999) found that HIF-1α mRNA is transiently induced in 3T3-L1 (L1) preadipocytes upon treatment with the adipogenic hormone cocktail containing insulin, dexamethasone and 3-isobutyl-1-methylxanthine (DM). However, the consequence of such transient HIF-1α expression was never investigated. Interestingly, adipogenesis can be inhibited by 2,3,7,8-tetrachlorodibenzo-p-dioxin (TCDD), which requires the aryl-hydrocarbon receptor (AhR), also a member of the bHLH-PAS family (Alexander et al., 1998; Phillips et al., 1995). Since AhR activates gene transcription by dimerization with HIF-1β (Probst et al., 1993), it is a reasonable hypothesis that inhibition of adipogenesis may be a function shared by some members of the bHLH-PAS family such as HIF-1α/β and AhR/HIF-1β.

Pathophysiological evidence exists that suggests a correlation between hypoxia and adipogenesis. For example, children with cyanotic heart disease have less body fat due to apparent adipocyte hypocellularity (Baum and Stern, 1977). High altitude training is well known to cause weight loss that is attributed in large part to body fat reduction (Armellini et al., 1997; Westerterp et al., 1994a). Strenuous physical training, on the other hand, is also attributed to significant loss of body fat (Van Etten et al., 1994; Westerterp et al., 1994b). Besides other physiological changes, hypoxia occurs in exercising skeletal muscles, as characterized by an increase in the expression of HIF-1 and VEGF (Gustafsson and Kraus, 2001; Gustafsson et al., 1999). Under hypoxia, fatty acid oxidation is impeded and glycolysis is augmented to maintain energy homeostasis. If the stored fat is not used under hypoxia, there is less need to increase or renew adipose tissue via adipogenesis. Experimentally, rats exposed to hypoxia experience significant fat loss (Mortola and Naso, 1997; Tanaka et al., 1997). Thus, reduction of adipose tissues can be caused by tissue hypoxia.

Adipocyte differentiation results from sequential induction of transcription factors C/EBPβ, C/EBPδ, PPARγ, and C/EBPα (Rangwala and Lazar, 2000; Rosen and Spiegelman, 2000). C/EBPβ and C/EBPδ are induced immediately but transiently upon IDM treatment to mediate the expression of PPARγ and C/EBPα (Christy et al., 1991; Wu et al., 1995; Yeh et al., 1995). In contrast to C/EBPδ, C/EBPβ is able to induce spontaneous differentiation in L1 cells and enhance the adipogenic potential in NIH-3T3 fibroblasts (Wu et al., 1995; Yeh et al., 1995). Highly specific for adipose tissues, PPARγ plays a critical role in the expression of most adipocyte-specific genes (Tontonoz et al., 1995) and is able to convert non-adipogenic mesenchymal cells such as fibroblasts and myoblasts to adipocytes (Hu et al., 1995; Tontonoz et al., 1994). Although developmentally necessary for adipogenesis (Wang et al., 1995b), C/EBPα is not always expressed during adipocyte differentiation especially in cells that already express C/EBPβ. For example, C/EBPα is not involved in the expression of GLUT-4, the insulin-responsive glucose transporter, in 3T3 cells ectopically expressing C/EBPβ and C/EBPδ (Wu et al., 1998). These data suggest the PPARγ and C/EBPβ may be potential targets for adipogenic intervention.

The effects of hypoxia are manifested by HIF-1 regulated genes. We and others have identified a hypoxia-induced gene DEC1/Stra13, a member of the *Drosophila* hairy/Enhancer of split (HES) family of bHLH transcription factors (Ivanova et al., 2001). The HES proteins play important roles in cell differentiation by repressing gene expression (Kageyama and Ohtsuka, 1999; Staal et al., 2001). During embryonic development, DEC1/Stra13 is expressed in neuroectoderm, and in some mesoderm and endoderm derived structures (Boudjelal et al., 1997). In P19 embryonal carcinoma cells, overexpression of DEC1/Stra13 promotes neuronal differentiation and inhibits mesodermal and endodermal differentiation (Boudjelal et al., 1997). In differentiating L1 cells, DEC1/Stra13 expression is increased approximately 2-fold within 1 hr of IDM treatment, followed by a rapid decrease within 24 hr (Inuzuka et al., 1999). At present, the role of DEC1/Stra13 during adipogenesis is ill defined.

Given the importance of $O_2$ sensing in embryonic development, as well as energy homeostasis and cell differentiation, $O_2$ tensions may control adipose tissue function by regulating adipogenesis. Since fatty acid metabolism requires mitochondrial respiration, hypoxia prevents the use of fatty acids and thus may obviate the need for more adipose tissue. Therefore, we have investigated whether hypoxia inhibits adipogenesis through the HIF-1 dependent induction of the DEC1/Stra13 gene expression. As mentioned above, adipocyte differentiation in vitro is determined by precisely orchestrated expression of the C/EBPs and PPARγ. We have thus determined whether the C/EBP family or PPARγ is the critical target of DEC1/Stra13, and whether overexpression of DEC1/Stra13 is sufficient to inhibit adipocyte differentiation. The regulation of adipogenesis by hypoxia opens new directions for research in understanding how the microenvironment regulates cell differentiation both under physiological settings as well as during the malignant progression of tumors.

SUMMARY OF THE INVENTION

Cellular differentiation involves transcriptional responses to environmental stimuli. Adipocyte differentiation is inhibited under hypoxic conditions, indicating that oxygen ($O_2$) is an important physiological regulator of adipogenesis. Hypoxia inhibits PPARγ2 nuclear hormone receptor transcription and overexpression of PPARγ2 or C/EBPβ stimulates adipogenesis under hypoxia. Mouse embryonic fibroblasts deficient in hypoxia-inducible transcription factor-1α (HIF-1α) are refractory to hypoxia-mediated inhibition of adipogenesis. The HIF-1 regulated gene DEC1/Stra13, a member of the *Drosophila* hairy/Enhancer-of-split transcription repressor family, represses PPARγ2 promoter activation and functions as an effecter of hypoxia-mediated inhibition of adipogenesis. These data indicate that an $O_2$-sensitive signaling mechanism regulates adipogenesis.

Thus, in some non-limiting embodiments of the present invention, agents that regulate HIF-1 activity or $O_2$-sensing may be used to inhibit adipogenesis and control obesity. For example, a cell may be contacted with a molecule that inhibits PPARγ2 transcription and/or activity. These molecules may act by directly inhibiting PPARγ2 transcription (e.g. the molecule binds to the PPARγ2 promoter, thereby hindering transcription factor access) or translation (e.g. the molecule is an antisense PPARγ2 nucleic acid). Alternatively, these molecules may be PPARγ2 agonists or antagonists. These molecules may also act indirectly by stimulating and/or activating DEC1/Stra13.

In some preferred embodiments, the invention provides a DEC1/Stra13 agonist comprising a truncated DEC1/Stra13 polypeptide lacking the DEC1/Stra13 repressor domain wherein the truncated polypeptide has substantially the same PPARγ2 promoter repressing activity as full-length DEC1/Stra13 polypeptide. A DEC1/Stra13 agonist of the invention preferably comprises the basic helix loop helix domain of DEC1/Stra13. DEC1/Stra13 agonist of the invention may have an amino acid sequence selected from the group consisting of amino acids 1-141 of SEQ ID NO:2, amino acids 1-141 of SEQ ID NO:4, and amino acids 1-141 of SEQ ID NO:7. A nonlimiting example of a DEC1 agonist of the invention is a truncated DEC1 polypeptide having substantially the same PPARγ2 promoter repressing activity as a full-length DEC1 polypeptide, wherein the truncated polypeptide consists essentially of a polypeptide having the amino acid sequence of amino acids 1-141 of SEQ ID NO:2. A nonlimiting example of a Stra13 agonist of the invention is a truncated Stra13 polypeptide having substantially the same PPARγ2 promoter repressing activity as a full-length Stra13 polypeptide, wherein the truncated polypeptide consists essentially of a polypeptide having the amino acid sequence of amino acids 1-141 of SEQ ID NO:4. The invention further provides isolated nucleic acids encoding a truncated DEC1/Stra13 polypeptide lacking the DEC1/Stra13 repressor domain wherein the truncated polypeptide has substantially the same PPARγ2 promoter repressing activity as full-length DEC1/Stra13 polypeptide.

In further non-limiting embodiments of the invention, agents that regulate HIF-1 activity or $O_2$-sensing may be used to inhibit angiogenesis and treat cancer. These embodiments are based, in part, on the observations that (a) hypoxia and DEC1/Stra13 overexpression inhibits transcription of PPARγ2; (b) PPARγ2 is localized in tumor endothelial cells (Inoue K et al., 2001); and (c) PPARγ2 knockout mice display reduced placental vascularization (Barak Y et al., 1999). Thus, without being restricted to any mechanism of action, Applicants hypothesize that hypoxia or agents that target HIF-1α, DEC1/Stra13, and/or PPARγ2 may inhibit angiogenesis and, therefore, may be used to treat cancer.

BRIEF DESCRIPTION OF THE DRAWINGS

The patent application file contains at least one drawing executed in color. Copies of this patent or patent application publication with color drawing(s) will be provided by the United States Patent and Trademark Office upon request and payment of the necessary fee.

(C) L1 cells were induced to differentiate under the following conditions: 20% $O_2$, 50 µM $CoCl_2$, or 100 µM DFO. Total RNA (5 µg/lane) was analyzed as in (A).

Figure 2:
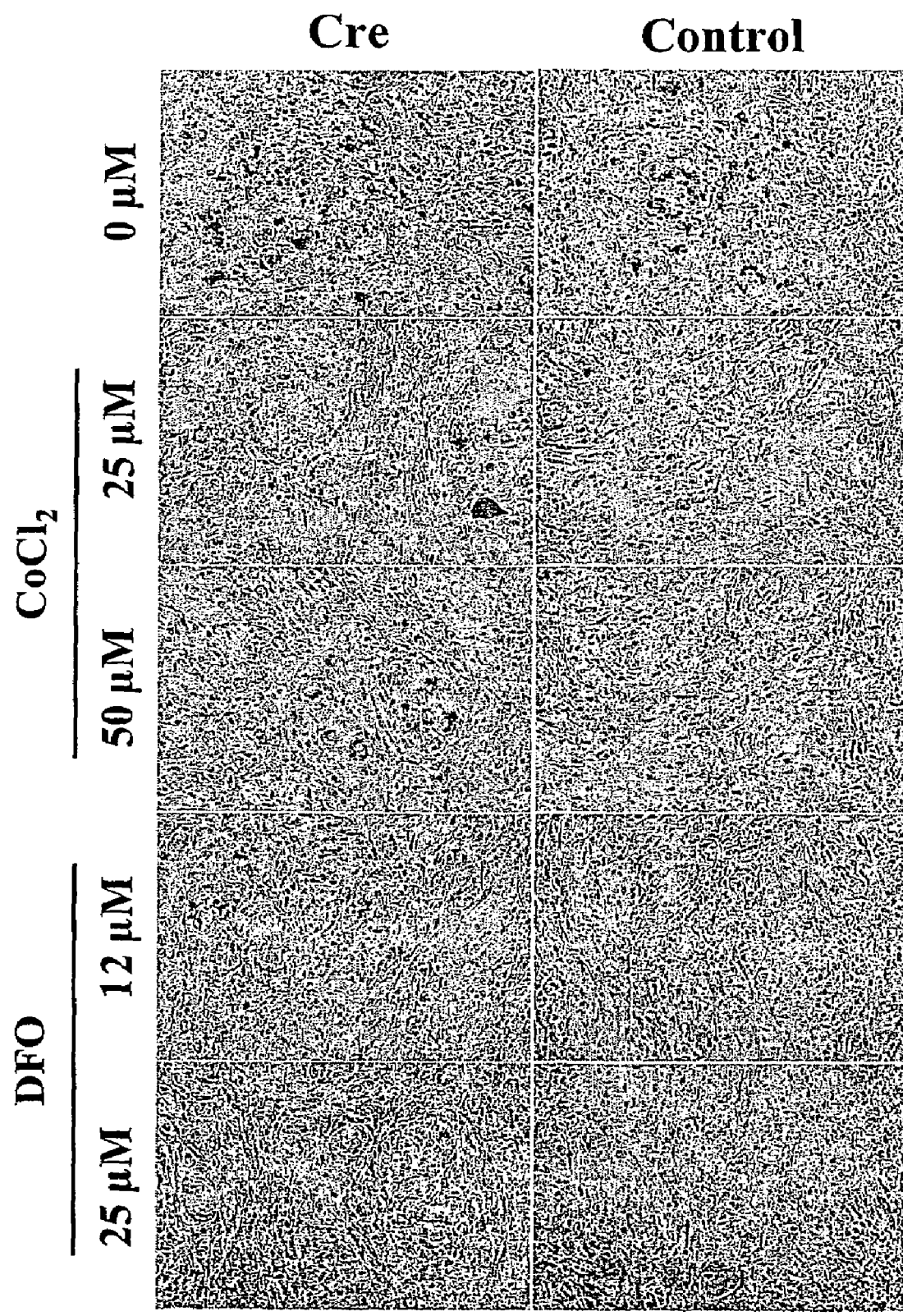
FIG. 2. HIF-1 is required for hypoxia-mediated inhibition of adipogenesis MEFs with HIF-1α alleles flanked by loxP sites were incubated with cre-adenovirus (Cre) or control adenovirus (Control) and induced to differentiate as described. $CoCl_2$ or DFO was added at the indicated final concentrations for the entire course of treatment. Cells were stained on Day 7 and photographed (×20).

(D) MEFs were treated as in FIG. 2. Total RNA was prepared 3 days after hormonal stimulation with or without 25 µM $CoCl_2$ or 12.5 µM DFO. Northern blotting analysis (10 µg/lane RNA) was done as in (A).

Figure 4:
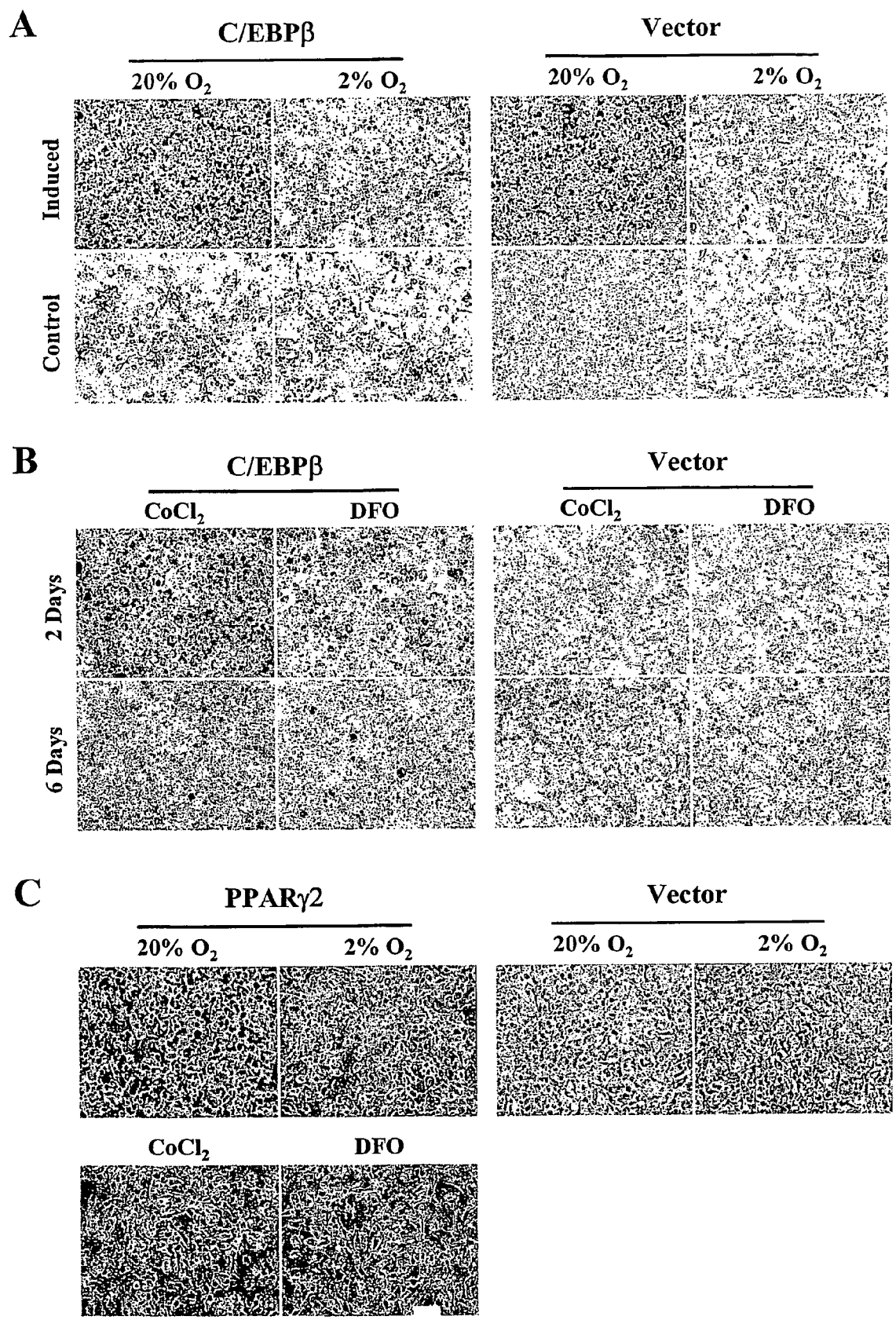

FIG. 4. Ectopic expression of C/EBPβ or PPARγ2 restores the adipogenic potentials of 3T3-L1 cells under hypoxia.

(A) Stable C/EBPβ- or vector-cells (L1) were induced to differentiate (Induced) or left uninduced (Control) either at 20% or 2% $O_2$. Cells were stained on Day 6 and photographed (×20).

(B) Stable C/EBPβ- or vector-cells (L1) were induced to differentiate at 20% $O_2$ in the presence of either 50 µM $CoCl_2$ or 100 µM DFO for the first 2 days of induction (2 Days) or the entire 6 days of treatment (6 Days). Cells were stained on Day 6 and photographed (×20).

(C) L1 cells transiently infected with PPARγ2 or vector control were induced to differentiate under the following conditions, 20% $O_2$, 2% $O_2$, 50 µM $COCl_2$ (6 days), or 100 µM DFO (6 days). Cells were stained on Day 6 and photographed (×20).

Figure 5:
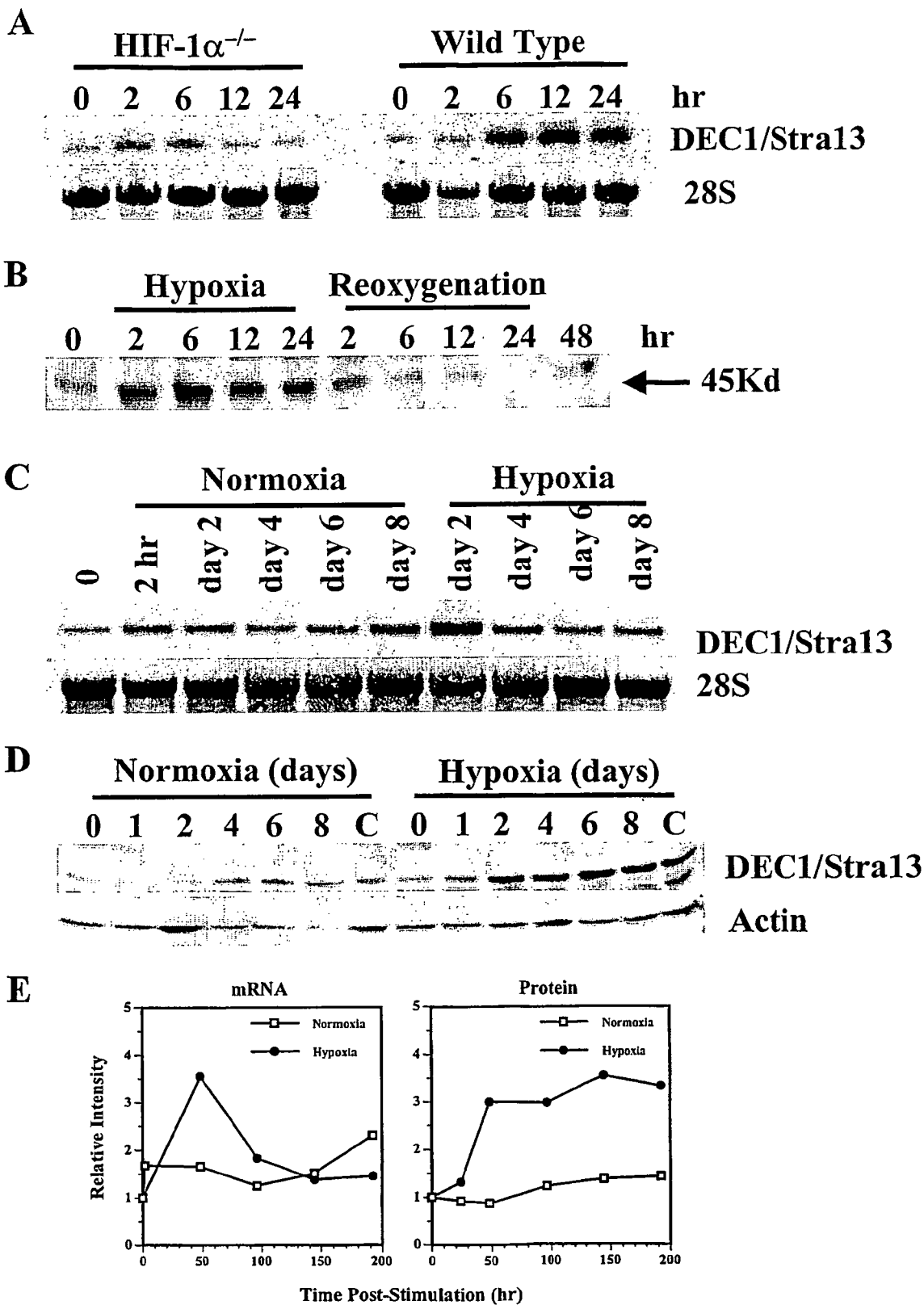

FIG. 5. DEC1/Stra13 expression is regulated by $O_2$ tensions via HIF-1

(A) Total RNA was prepared from HIF-1α$^{-/-}$ or wild-type MEF cells at indicated time at 0.01% $O_2$. Equal amounts (10 µg/lane) of total RNA were subjected to Northern blotting analysis with $^{32}$P-labeled Stra13 cDNA as probe.

(B) NIH-3T3 cell lysates were prepared at indicated time at 0.01% $O_2$ or during reoxygenation following 24 hr hypoxia. Normoxic controls were prepared at 0 hr and 48 hr, respectively. DEC1/Stra13 protein was analyzed by Western blotting (25 µg protein/lane) as described.

(C) L1 cells were induced to differentiate either under normoxia or hypoxia (0.01% $O_2$). Equal amounts (10 µg/lane) of total RNA prepared at indicated time after induction were subjected to Northern blotting as in (A). The relative levels of DEC1/Stra13 mRNA were analyzed by densitometry (E).

(D) L1 cells were induced to differentiate as in (C). Cell lysates were prepared at indicated times after treatment and subjected to Western blotting (20 µg protein/lane) as described. The controls (lane C) were maintained under either normoxia or hypoxia without adipogenic stimulation. The relative levels of DEC1/Stra13 protein were analyzed by densitometry (E).

Figure 6:
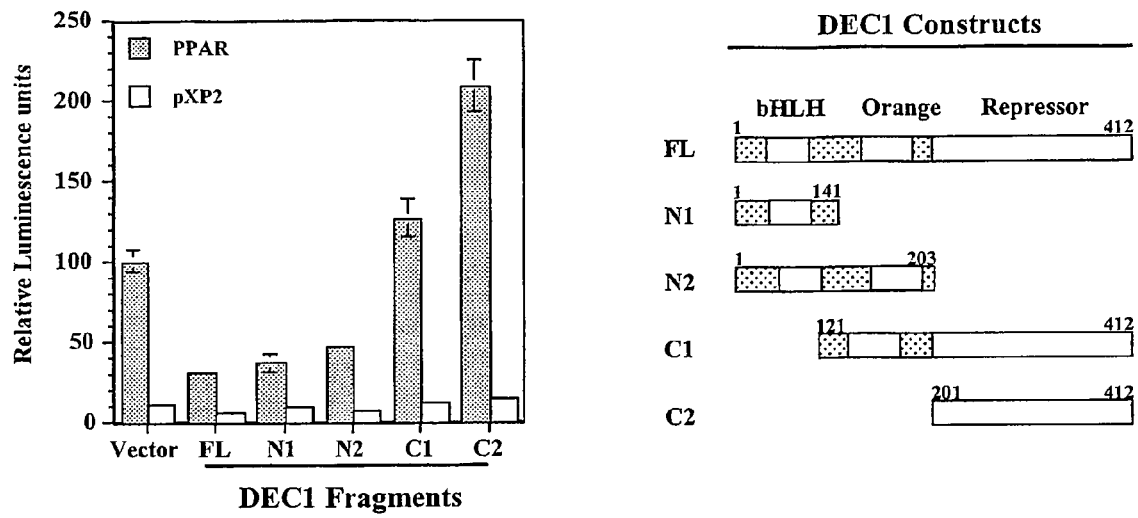
Figure 6:
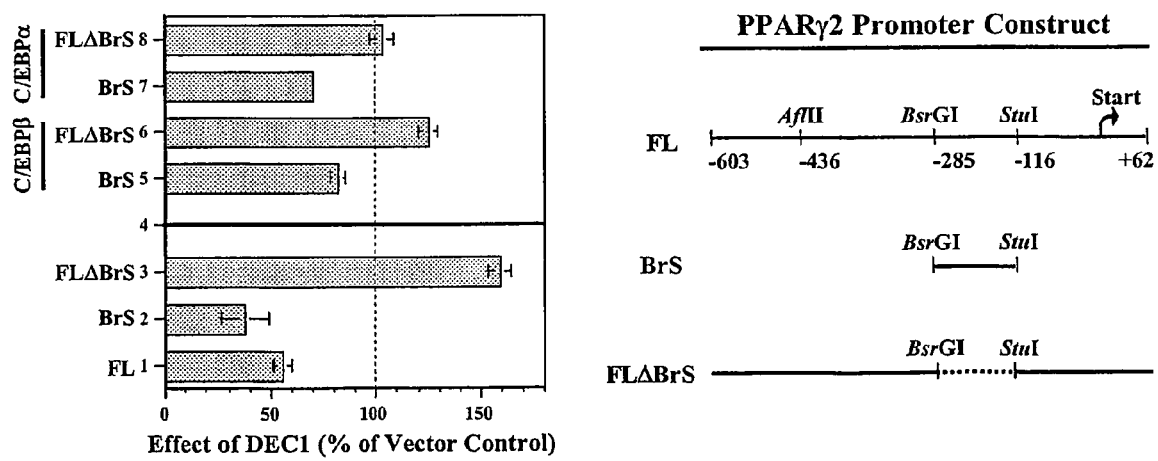
Figure 6:
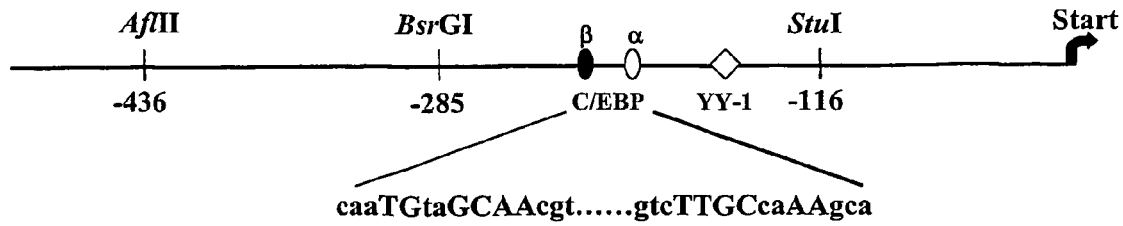

FIG. 6. DEC1/Stra13 represses PPARγ2 promoter activity (A) NIH-3T3 cells were transiently co-transfected with the 0.6-kb PPARγ2 promoter-driven luciferase construct (PPAR) or the promoter-less vector (pXP2) and DEC1 fragments (0.3 µg DNA each) as indicated. Luciferase activities in cell lysates were measured 40-48 hr after transfection using a luminometer and presented as relative luminescence units±s.d.

(B) Luciferase constructs (pXP2) with the 0.6-kb PPARγ2 promoter (FL), BsrGI-StuI fragment alone (BrS), or deletion of BsrGI-StuI fragment (FLΔBrS) were co-transfected into NIH-3T3 cells with DEC1 or its vector control at the ratio of 1:5 (DEC1 or control to pXP2). In other experiments, C/EBPα or C/EBPβ were also co-transfected at the ratio of 1:1 (C/EBP to pXP2). A Renilla luciferase construct was also included to monitor transfection efficiency. Luciferase activities were measured as in (A).

(C) Schematic representation of the PPARγ2 proximal promoter region. Putative C/EBP sites are displayed with the conserved bases capitalized.

Figure 7:
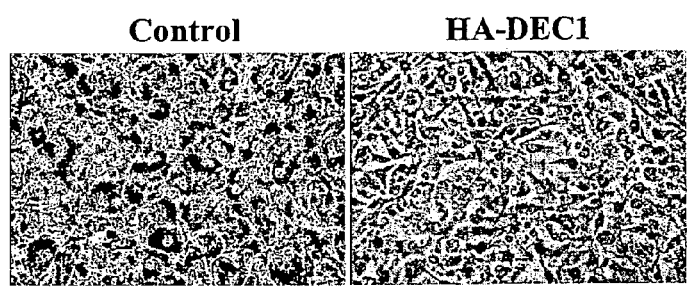
Figure 7:
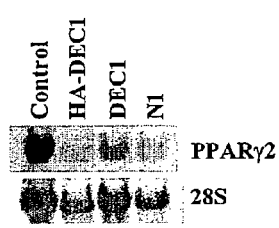
Figure 7:
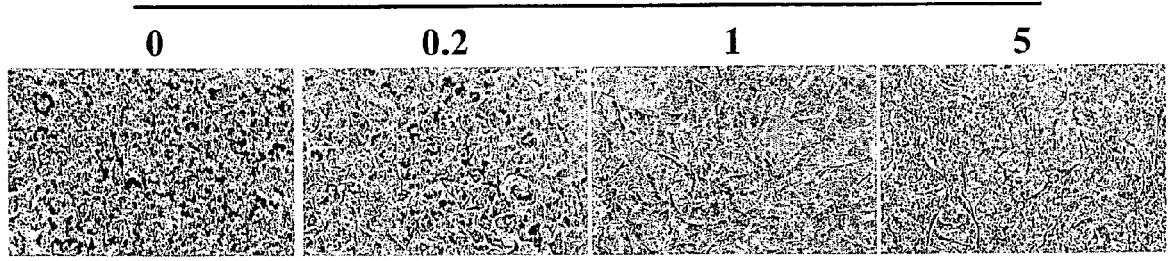

FIG. 7. Ectopic expression of DEC1/Stra13 inhibits differentiation of 3T3-L1 preadipocytes (A) L1 cells were retrovirally infected with HA-DEC1, DEC1, N1 or vector control (pLXSN) and then induced to differentiate as described. Oil Red O-stained cells were photographed (20×) on Day 5.

(B) L1 cells were retrovirally infected as in (A). Total RNA was isolated on Day 2 after IDM stimulation and was analyzed by Northern blotting as in FIG. 3A.

(C) L1 cells were induced to differentiate with or without the TAT-N1 (DEC1 aa1-141) protein at indicated final concentrations. Cells were stained on Day 6 and photographed (20×).

DETAILED DESCRIPTION OF THE INVENTION

Hypoxia Inhibits Adipogenesis via HIF-1

Figure 1:
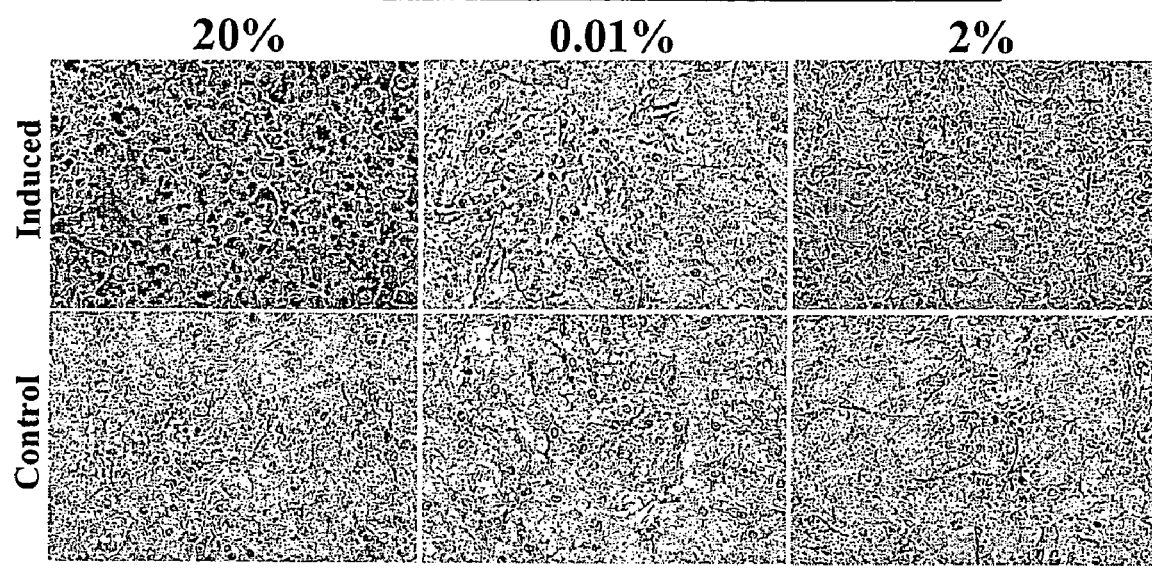
FIG. 1. Hypoxia inhibits adipogenesis
  (A) L1 cells were induced to differentiate (induced) or left uninduced (Control) at indicated $O_2$ tensions. Cells were stained on Day 6 with Oil Red O and photographed (×20).
  (B) L1 cells were induced to differentiate in the presence or absence of $CoCl_2$ (50 μM) or DFO (100 μM) for the first 2 days together with IDM, and then maintained in media without $CoCl_2$ or DFO. Cells were stained on Day 6 and photographed (×20).
  (C) MEFs were treated in DM containing 5 μM rosiglitazone with or without $CoCl_2$ (25 μM) or DFO (25 μM). Cells were stained on Day 6 and photographed (×20).
Figure 1:
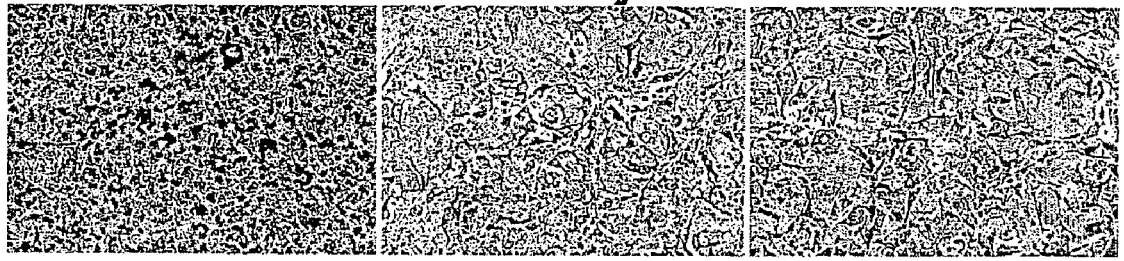
Figure 1:
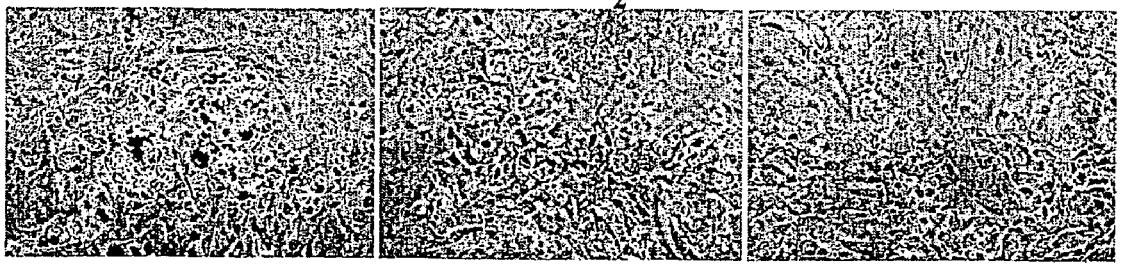

To evaluate the effect of hypoxia on adipogenesis, L1 cells were treated at different $O_2$ tensions with the standard cocktail of adipogenic hormones, IDM (FIG. 1A). Under normoxia (20% $O_2$), L1 cells differentiate into mature adipocytes loaded with fat droplets as indicated by Oil Red O staining. However, adipocyte differentiation is completely inhibited when L1 cells are induced to differentiate under hypoxia (0.01% or 2% $O_2$). No significant changes in cell death were detected in hypoxia-treated cells by the Trypan Blue exclusion assay when compared to the normoxic control. Hypoxic effects can be mimicked by iron-chelators (deferoxamine or DFO), or divalent transition-metal ions (cobalt). Inhibition of L1 cell differentiation is observed when $CoCl_2$ or DFO is added to the treatment media throughout the course of induction (6 days). However, treatment with $CoCl_2$ or DFO for the first 2 days of induction with IDM is sufficient to prevent L1 cell differentiation (FIG. 1B). Mouse embryonic fibroblast (MEF) cells were used to evaluate if the inhibition of adipogenesis by hypoxia was a general phenomenon. MEFs are induced to differentiate into adipocytes by IDM supplemented with 5 µM rosiglitazone, a synthetic PPARγ2 ligand (Lehmann et al., 1995). Consistent with the literature, about 15-20% of the MEF cells differentiate into adipocytes (Alexander et al., 1998). Treatment of MEPs with $CoCl_2$ or DFO suppresses adipogenesis (FIG. 1C). Similar observations are made when MEF cells are maintained under at 2% $O_2$.

To assess the role of HIF-1 in the inhibition of adipogenesis, MEFs in which each allele of HIF-1 a was flanked by loxP sites were used (Ryan et al., 2000). The HIF-1α gene is efficiently excised when MEFs are transduced with adenovirus containing the cre recombinase gene (Seagroves et al., 2001). Both cre-treated and control MEF cells differentiate into adipocytes upon hormonal stimulation in the absence of hypoxia mimetics (FIG. 2). When the HIF-1α gene is deleted from the genome by cre, the HIF-1α deficient MEF cells continue to undergo significant adipocyte differentiation in the presence of either $CoCl_2$ (up to 50 µM) or DFO (up to 25 µM) (FIG. 2). In contrast, $CoCl_2$ or DFO significantly represses differentiation of the control-treated MEF cells under the same conditions (FIG. 2). This result indicates that HIF-1 is involved in inhibition of adipogenesis by hypoxia.

Hypoxia Inhibits Induction of PPARγ2 Expression

Figure 3:
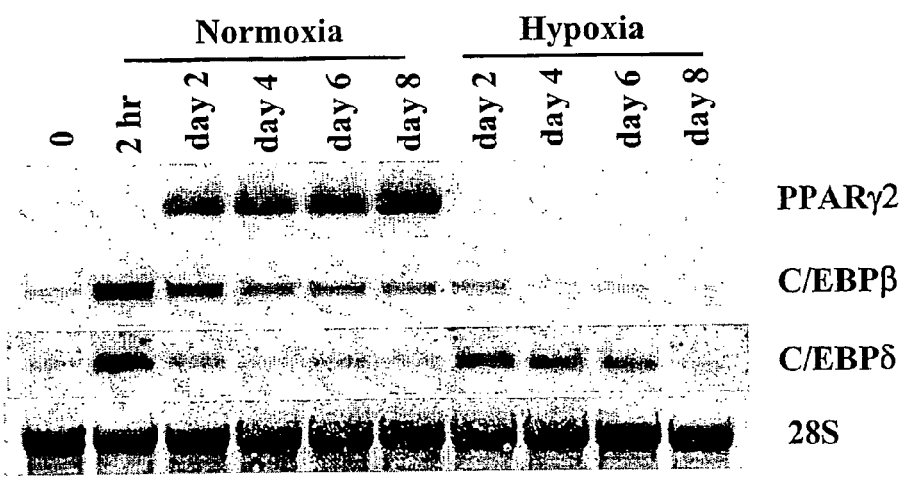
FIG. 3. Hypoxia modulates the expression of PPARγ2, C/EBPβ and C/EBPδ
  (A) and (B) L1 cells were induced to differentiate either under normoxia or hypoxia (0.01% $O_2$). Total cellular RNA was prepared at indicated times after induction. Equal amounts (10 µg/lane) of total RNA were subjected to Northern blotting (A) using $^{32}$P-labeled PPARγ2, C/EBPβ or C/EBPδ cDNA as probes. The relative levels of expression were analyzed by densitometry (B).
Figure 3:
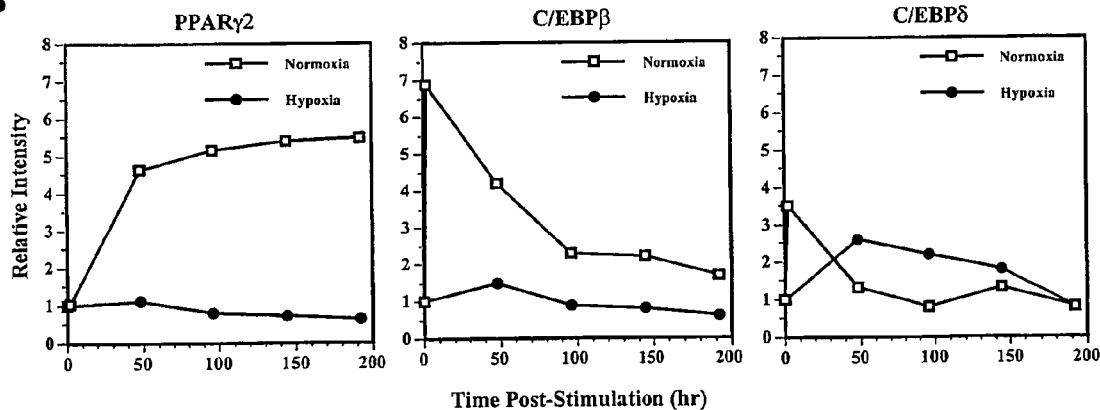
Figure 3:
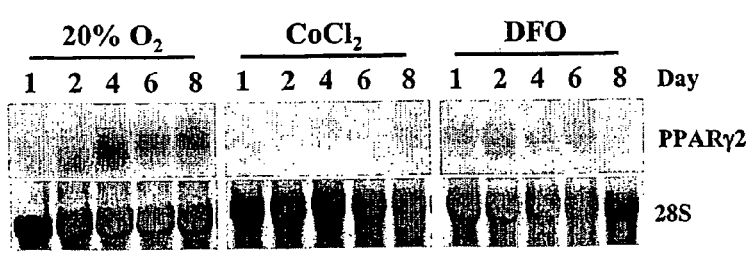
Figure 3:
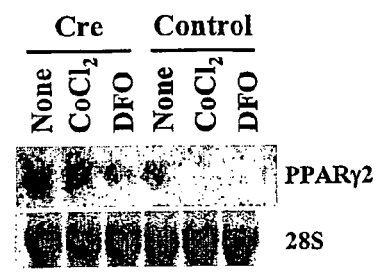

The effect of hypoxia on the expression of three key transcription factors, C/EBPβ, C/EBPδ and PPARγ, during L1 differentiation was investigated (Rangwala and Lazar, 2000; Rosen and Spiegelman, 2000). At 20% $O_2$, both C/EBPβ and C/EBPδ are significantly induced within 2 hr of IDM treatment, followed by their gradual decrease (FIGS. 3A and B). PPARγ2 mRNA is induced by Day 2 post-IDM treatment following the expression of C/EBPβ and C/EBPδ, and remains elevated throughout the rest of the differentiation process (FIGS. 3A and B). Under hypoxia, the induction of PPARγ2 expression is completely abolished, and that of C/EBPβ is reduced (FIGS. 3A and B). The PPARγ2 expression is also repressed in L1 cells treated with $CoCl_2$ or DFO (FIG. 3C). Unexpectedly, C/EBPδ expression becomes dysregulated and its mRNA remains elevated under hypoxia (FIGS. 3A and B). To assess the role of HIF-1 in PPARγ2 inhibition, the PPARγ2 mRNA in MEFs that were treated with cre to excise the HIF-1α alleles were analyzed. As shown in FIG. 3D, PPARγ2 induction is protected in cre-treated MEFs, but not in mock-treated cells, indicating that HIF-1 is required for the inhibition of PPARγ2 expression. These results suggest that negative regulation of PPARγ2 and/or C/EBPβ gene expression is a key mechanism for hypoxia-mediated inhibition of adipogenesis.

We next investigated whether overexpression of C/EBPβ gene was sufficient to restore L1 cell differentiation under hypoxia. Consistent with the literature (Yeh et al., 1995), C/EBPβ-expressing L1 cells display much higher levels of differentiation than the vector-infected cells with or without stimulation by IDM under normoxic conditions (FIG. 4A). At 2% $O_2$, the C/EBPβ-expressing cells continue to differentiate into adipocytes, independent of IDM treatment (FIG. 4A). However, the differentiation of the vector-infected cells is completely inhibited at 2% $O_2$. When hypoxia mimetics are used, the continuous presence of $CoCl_2$ or DFO is necessary for significantly reducing differentiation and/or fat accumulation of the C/EBPβ-expressing L1 cells (FIG. 4B). If $CoCl_2$ or DFO is present for the first 2 days of adipogenic induction, the C/EBPβ-expressing L1 cells are still able to differentiate into fat-laden adipocytes (FIG. 4B). Thus, while overexpression of C/EBPβ can make L1 cells refractory to hypoxia or hypoxia mimetics, the level of adipocyte differentiation induced by IDM in these same cells is attenuated. This result suggests that hypoxia may be affecting additional modulators of adipogenesis induced by IDM.

We also determined whether overexpression of PPARγ2 gene is sufficient to drive L1 differentiation under hypoxia. L1 cells received three rounds of PPARγ2 retroviral gene infection to maximize infection efficiency. The PPARγ2-infected cells are induced to differentiate in medium containing 10% fetal bovine serum and 1 μM rosiglitazone. Significant adipocyte differentiation is observed at 20% $O_2$ (FIG. 4C), indicating efficient expression of PPARγ2 gene. In contrast, vector-infected L1 cells do not differentiate under the same conditions although these cells can still differentiate upon IDM-stimulation. Similar to C/EBPβ-transduced cells, the majority of the PPARγ2-expressing cells differentiate into adipocytes when stimulated by rosiglitazone under the conditions of 2% $O_2$, $CoCl_2$, or DFO but they accumulate less fat as compared to normoxic controls (FIG. 4C). Our results indicate that overexpression of PPARγ2 or C/EBPβ gene can overcome inhibition of adipocyte differentiation under hypoxia, but the phenotype of mature adipocytes is not fully restored.

DEC1/Stra13 is an Effector for Hypoxia-Mediated Inhibition of Adipogenesis

Since HIF-1 is a transcription activator, the inhibition of adipogenesis by hypoxia is likely to be mediated by HIF-1 regulated genes. We investigated whether the HIF-1 target gene DEC1/Stra13, which contains a bHLH and an Orange domain homologous to those of the HES transcription repressors (Boudjelal et al., 1997; Shen et al., 1997), is involved in inhibition of adipogenesis by hypoxia. HIF-1 is required for hypoxic induction of DEC1/Stra13 since the increase of DEC1/Stra13 mRNA occurs in wild-type MEF cells, but not in HIF-1α$^{-/-}$ MEF cells (FIG. 5A). DEC1/Stra13 protein is also sensitive to $O_2$ tensions as it increases rapidly under hypoxia and decreases to its basal level within 6-12 hr upon reoxygenation (FIG. 5B). During L1 cell differentiation under normoxia, DEC1/Stra13 mRNA is induced approximately 2 fold within 2 hr of IDM treatment (FIGS. 5C and E), which is consistent with the literature (Inuzuka et al., 1999). In contrast, DEC1/Stra13 mRNA in differentiating L1 cells exhibits approximately a 4-fold increase on Day 2, followed by a steady decline to the basal level under hypoxia (FIGS. 5C and E). Interestingly, the DEC1/Stra13 protein level remains elevated (approximately 3 fold) from Day 2 through Day 8 under hypoxia as compared to normoxia (FIGS. 5D and E). The increased stability of DEC1/Stra13 protein in IDM-stimulated L1 cells indicates that both DEC1/Stra13 mRNA and protein are regulated by hypoxia.

To address whether DEC1/Stra13 could repress PPARγ2 gene induction, the effect of DEC1 on the PPARγ2 promoter activity was analyzed using the 0.6-kb PPARγ2 promoter (−603 to +62)-driven luciferase gene as a reporter for PPARγ2 transcriptional activity (Tong et al., 2000). As shown in FIG. 6A, full-length DEC1 represses PPARγ2 promoter activity by 70% as compared to the vector control. Interestingly, two N-terminal fragments (N1 and N2) containing the bHLH domain show similar levels of repression as the full-length DEC1 (FIG. 6A). In contrast, the two C-terminal fragments (C1 and C2) do not inhibit PPARγ2 promoter activity. This result suggests that the bHLH domain of DEC1/Stra13 is functionally sufficient for inhibition of PPARγ2 gene expression. Using a series of deletion or truncation constructs of the 0.6-kb PPARγ2 promoter (FL), the BsrGI (−285)-StI (−116) fragment (BrS) was found to contain the element(s) repressible by DEC1. Compared to the FL promoter, the BrS fragment shows similar levels of repression by DEC1, whereas the region with BrS deleted (FLΔBrS) is no longer repressed by DEC1 (FIG. 6B). Structural analysis suggests a C/EBPβ site at −229 (SEQ ID NO:5) and a C/EBPα site at −200 (SEQ ID NO:6) followed by a YY-1 box within BrS (FIG. 6C). Co-transfection of C/EBPβ or a can partially relieve repression by DEC1 (FIG. 6B). Further deletion of the C/EBPβ site or both C/EBP sites from BrS results in 80% and 85% decrease in transcription activity alone, respectively. Together, these data suggest that DEC1 repression is mediated, at least in part, by the putative C/EBP sites at −229 and −200.

More importantly, overexpression of DEC1 or HA-DEC1 in L1 cells by retroviral infection results in nearly complete inhibition of adipocyte differentiation (FIG. 7A). Significant inhibition is also conferred by retroviral transduction of N1 (amino acid or aa1-141), as shown in FIG. 7A. Inhibition of adipogenesis by DEC1 is consistent with the finding that PPARγ2 expression is repressed in L1 cells ectopically expressing DEC1, HA-DEC1 or N1 (FIG. 7B). As shown in FIG. 6A, the bHLH domain of DEC1/Stra13 is functionally equivalent to the full-length protein in repressing PPARγ2 expression. To more vigorously investigate the role of this bHLH domain in regulating adipogenesis, a fusion protein between N1 and an 11-aa protein transduction domain (YGRKKRRQRRR; SEQ ID NO:7) derived from the TAT protein of human immunodeficiency virus (HIV) was constructed (Schwarze and Dowdy, 2000). A dose dependent inhibition of adipogenesis is found when L1 cells are induced to differentiate in the presence of the TAT-N1 fusion protein (FIG. 7C). These results indicate that DEC1/Stra13 functions as an effecter of HIF-1 for the inhibition of adipogenesis by hypoxia.

Our results indicate that hypoxia-mediated adipogenic inhibition involves the repression of PPARγ2 gene induction and decrease in C/EBPβ expression, two critical events during adipogenesis. The inhibition of PPARγ2 expression and its activity is a common mechanism for adipogenic inhibition by a variety of stimuli. A recent report has shown that HIF-1 can also repress PPARα gene expression (Narravula and Colgan, 2001). However, PPARα may only play a minor role in white adipose tissue or preadipocytes as suggested by its low abundance (Braissant et al., 1996) and by gene knockout studies (Lee et al., 1995). The transcriptional activity of PPARγ2 protein is inhibited when phosphorylated by the mitogen-activated protein kinase (MAPK) (Hu et al., 1996). Expression of PPARγ2 is repressed by the zinc-finger family transcription factors GATA-2 and GATA-3 that are expressed in preadipocytes but dissipate at the onset of adipogenic stimulation (Tong et al., 2000). Constitutive expression of GATA-2 or -3 prevents adipogenesis by inhibiting PPARγ2 expression. Nevertheless, expression of PPARγ2 fails to completely rescue the adipogenic inhibition by GATA-2 or -3. Wnt-mediated signaling also inhibits the expression of PPARγ2 and C/EBPα and thereby represses the adipogenesis (Ross et al., 2000). Co-expression of PPARγ2 or C/EBPα with Wnt, again, does not fully restore adipogenesis. Similar to these observations, expression of PPARγ2 can only partially restore the differentiation of L1 preadipocytes under hypoxia. These findings suggest that other PPARγ2-independent mechanisms also play important roles during adipocyte differentiation.

Retinoic acid (RA) inhibits the expression of PPARγ and C/EBPα without affecting C/EBPβ expression (Schwarz et al., 1997). Overexpression of C/EBPα or C/EBPβ does not overcome RA-mediated inhibition. It is interesting to note that DEC1/Stra13 gene expression can also be induced by RA (Boudjelal et al., 1997), as well as by hypoxia, suggesting that DEC1/Stra13 mediates repression of PPARγ2, but not. C/EBPβ. Thus, the similarity between RA- and hypoxia-mediated adipogenic inhibition supports a role for DEC1/Stra13 as a common effecter of both RA- and hypoxia-induced inhibition of adipocyte differentiation.

DEC1/Stra13 is well implicated in cell differentiation. DEC1 was identified in differentiating human embryonic chondrocytes stimulated by a cyclic AMP analog (Shen et al., 1997). Its mouse homologue, Stra13 (97% identical at protein level), was identified during the RA-induced neuronal differentiation of P19 embryonal carcinoma cells (Boudjelal et al., 1997). In L1 cells, rapid but transient induction of Stra13 mRNA was found upon IDM stimulation (Inuzuka et al., 1999), which may be important in temporally regulating transcription for adipogenesis. The regulation of the PPARγ2 promoter is still not understood and seems quite complex. The data presented in the instant disclosure suggest that DEC1/Stra13 represses the activation of PPARγ2 promoter potentially via the putative C/EBP sites at −229 and −200. However, unlike other members of the HES family, DEC1/Stra13 does not bind to the E-box (CANNTG), the N-box (CACNAG), or the related C-box (CACGCG). It is unlikely that DEC1/Stra13 binds any C/EBP site directly. Nevertheless, it is possible that DEC1/Stra13 may function through interaction with other transcription factors such as TBP, TFIIB, and USF (Boudjelal et al., 1997; Dhar and Taneja, 2001). The exact nature of DEC1/Stra13-mediated inhibition of PPARγ$^2$ transcription warrants further investigation.

DEC1/Stra13 protein remains elevated in L1 cells under hypoxia even after its mRNA level decreases to the basal level. Such exceptional protein stability can potentially explain the incomplete recovery of adipogenesis under hypoxia even when PPARγ or C/EBPβ is overexpressed. The mechanism for increased protein stability of DEC1/Stra13 warrants additional studies as it belongs to a small of group of proteins including HIF-1α and p53 that are regulated at the protein level under hypoxia (Graeber et al., 1994; Jewell et al., 2001). Preliminary examination suggests that each of the changes in stabilization of these proteins under hypoxia occurs by a different mechanism (Alarcon et al., 1999; Semenza, 1999; Z. Yun and A. J. Giaccia, unpublished observations).

In addition to the adipogenic hormones, the adipocyte microenvironment such as the extracellular matrix (Selvarajan et al., 2001) can also have significant influence on adipogenesis. The data presented in the instant disclosure strongly suggest that hypoxia, a physiological factor of the tissue microenvironment, may be an important regulator of adipogenesis. The importance of HIF-1 on adipocyte differentiation extends its role in regulating energy homeostasis. This mechanism of adipogenic repression may be potentially useful for controlling obesity by the regulation of HIF-1, DEC1/Stra13 or pharmacological manipulation of intracellular $O_2$-sensing mechanisms.

In some embodiments of the invention, a mammalian cell or tumor may be contacted with an agent that directly or indirectly reduces the amount of active PPARγ2 in a nucleus, a cell, and/or a tumor, which may result in inhibition of angiogenesis. Non-limiting examples of agents that may be used include DEC1/Stra13 polypeptides (truncated or full-length), retinoic acid, antisense PPARγ2, anti-PPARγ2 antibodies (mono- or polyclonal), and thiazolidinediones or combinations thereof. Artisans of ordinary skill may determine the amount of the agent necessary to result in inhibition of angiogenesis by either directly assaying the agent's effect on angiogenesis or by assaying the agent's effect on PPARγ2 levels using any angiogenesis or PPARγ2 assays known in the art. A non-limiting example of an angiogenesis assay is described in O'Reilly et al. 1994. Nonlimiting examples of methods of assaying PPARγ2 levels include Mueller et al., 1998 and Palakurthi et al. 2001.

Agents of the invention may be administered for antiadipogenesis or antiangiogenesis by injection or gradual infusion subcutaneously, intraocularly, intravenously, intramuscularly, intracavity, orally, or transdermally. A therapeutically effective amount of an antiangiogenesis agent is the amount necessary to result in a measurable inhibition of either de novo angiogenesis or growth factor stimulated angiogenesis. A therapeutically effective amount of an antiadipogenesis agent is the amount necessary to result in a measurable inhibition of adipogenesis.

For thiazolidinediones, the concentration may be less than about 10 μM (Berger et al. 2002) and may be up to about three orders of magnitude less than 10 µM. A truncated DEC1/Stra13 protein may be used at from about 0.2 µM to about 5 µM.

Agents of the invention may be used to inhibit angiogenesis in cells associated with any tumor. Nonlimiting examples of tumors that may be susceptible to antiangiogenic treatment include tumors of the colon, breast, and prostate. Nonlimiting examples further include tumors of the bladder, brain, cervix, connective tissue, endometrium, esophagus, liver, kidney, lung, lymph node, ovary, skin, intestine, stomach, testis, and uterus. Agents of the invention may also be used to for treatment of angiogenic dependent or angiogenic associated diseases, such as diabetic retinopathy, obesity, macula degeneration, rheumatoid arthritis, graft rejection such as corneal or kidney graft, angiomas, angiosarcomas, and Castelman disease and Kaposi sarcoma.

The invention provides methods of inhibiting angiogenesis in a tumor comprising contacting at least one cell of a tumor with a therapeutically effective amount of an agent of the invention selected from the group consisting of a DEC1/Stra13 polypeptide (truncated or full-length), retinoic acid, an antisense PPARγ2 nucleic acid, an anti-PPARγ2 antibody (mono- or polyclonal), and a thiazolidinedione.

EXAMPLES

The examples provided in the instant disclosure are intended to further illustrate the invention and, therefore, shall not be construed to limit the scope of the instant invention.

Example I

Reagents

Cobalt Chloride ($CoCl_2$), deferoxamine mesylate (DFO), Oil Red O, insulin (INS), dexamethasone (DEX), and 3-isobutyl-1-methylxanthine (MIX) were purchased from Sigma (St. Louis, Mo.). Stock solution of rosiglitazone was prepared in dimethylsulfoxide (DMSO) from the Avandia™ tablets (GlaxoSmithKline Pharmaceuticals).

Example II

Plasmids

The following constructs were made by PCR amplification of cDNA fragments using pGEM-DEC1 (T. Kawamoto, Hiroshima University, Japan) as template and in-frame cloning at the EcoRI into pcDNA3.1His or pLXSN: pLXSN-DEC1, pLXSN-DEC1 aa1-141 (N1), pcDNA3.1-DEC1, pcDNA3.1-DEC1 aa1-141 (N1), pcDNA3.1-DEC1 aa1-203 (N2), pcDNA3.1-DEC1 aa121-412 (C1), and pcDNA3.1-DEC1 aa201-412 (C2). The TAT-N1 was constructed by PCR amplification of DEC1 aa1-141 and cloned in frame at the EcoRI into pTAT-HA (S. F. Dowdy, Washington University, St. Louis, Mo.). The pLXSN/HA-DEC1 was made as follows. Full-length DEC1 was PCR-amplified with 5' NheI and 3' XbaI, and was cloned into pAS1 at the NheI in frame to the HA tag. The pAS1-DEC1 was cut with NdeI, filled-in by Klenow, and then cut with EcoRI to release the HA-tagged DEC1. Finally, the HA-tagged DEC1 was ligated into the pLXSN prepared by XhoI digest, Klenow fill-in, and then EcoRI digest. The following PPARγ2 promoter constructs were made from pXP2-PPARγ2 (−603 to +62) (G. S. Hotamisligil, Harvard University, Boston, Mass.) by restriction digest, Klenow fill-in, and then ligation: BsrGI (−285)-StuI (−116) fragment (BrS) and deletion of BsrGI-StuI fragment (FLΔBrS). All constructs were verified by sequencing.

Example III

Cell Culture

NIH-3T3 (ATCC, Rockville, Md.), HIF-1α$^{-/-}$ mouse embryonic fibroblasts (MEFs) (Ryan et al., 1998), wild-type MEFs, and MEFs with HIF-1α alleles flanked by loxP sites (Ryan et al., 2000) were cultured in Dulbecco's modified Eagle's medium (DMEM) supplemented with 10% fetal bovine serum (FBS), penicillin and streptomycin. 3T3-L1 preadipocytes (ATCC) were maintained in growth medium (GM) containing 10% bovine calf serum (ATCC) and 1 mM sodium pyruvate in DMEM.

Example IV

Adipocyte Differentiation and Oil Red O Staining

Based on previously described procedure (Wu et al., 1996), L1 cells were maintained in GM for 2 days after confluence. The confluent cells were treated (day 0) with differentiation medium (DM) containing 10% FBS, 10 µg/ml INS, 1 µM DEX and 0.5 mM MIX in DMEM for 2 days. Cells were then maintained in DMEM containing 10% FBS and 1 µg/ml INS, and the medium was replaced every other day.

MEFs were induced to differentiate 2 days after confluence (day 0) with DM supplemented with 5 µM rosiglitazone (Alexander et al., 1998; Lehmann et al., 1995). The medium was replaced on Day 3 with DMEM plus 10% FBS, 1 µg/ml INS and 5 µM rosiglitazone, and was then changed every other day. To remove the HIF-1α gene, subconfluent culture of MEFs with HIF-1α alleles flanked by loxP sites were treated with adenovirus containing cre recombinase or control adenovirus at the multiplicity of infection (MOI) of 50 as previously described (Seagroves et al., 2001). The treated MEF cells were grown to confluence for 2 days before they were induced to differentiate as above.

To evaluate the effects of hypoxia on adipogenesis, cells were maintained at 20% $O_2$ in standard incubator, 2% $O_2$ in standard incubator or 0.01% $O_2$ in an anaerobic chamber immediately following treatment with DM. Alternatively, $CoCl_2$ or DFO was added to DM at indicated concentrations either during the initial stage of stimulation or for the entire course of differentiation.

For visualization of differentiated adipocytes, cells were washed with phosphate-buffered saline (PBS) and stained in 60% of the Oil Red O stock solution (0.5 g Oil Red O in 100 ml of isopropanol) for 30 min at 37° C. Cells were briefly washed in 60% isopropanol and then rinsed in distilled water for microscopic observation and photography.

Example V

Retroviral Infection of 3T3-L1 Cells

Retroviruses were produced using the phoenix cell system (Baker et al., 1992; Pear et al., 1993). L1 cells at 30-50% confluence were retrovirally infected 2-3 times with 8 µg/ml Polybrene by centrifugation at 1800-2000 rpm for 1 hr, followed by overnight incubation at 32° C. For generation of stable C/EBPβ-expressing cells, L1 cells were infected with pBABEpuro or pBABEpuro-C/EBPβ (S. R. Farmer, Boston University, Boston, Mass.), followed by selection with 1 µg/ml of puromycin (Sigma). The stable cells were grown to confluence and induced to differentiate as described above. For transient infection with pBABEpuro, pBABEpuor-PPARγ2 (B. M. Spiegelman, Harvard University, Boston, Mass.), pLXSN/HA-DEC1, pLXSN-DEC1 and pLXSN-N1, L1 cells were spin-infected and induced to differentiate as described above.

Example VI

Northern and Western Blotting Analysis

Total cellular RNA was isolated with Trizol reagent (Life Technologies). The following plasmids were used for cDNA template preparations by restriction digest: MSV-C/EBPβ and MSV-C/EBPδ (S. L. McKnight, Univ. Texas Southwestern Medical Center, Dallas, Tex.), pSVsport-PPARγ2 (B. M. Spiegelman), pBS-Stra13 (P. Chambon, INSERM, Strasbourg, France). Hybridization was carried out at 65° C. for 6 to 12 hr. The radioactive blot was visualized on Storm 860 PhosphoImager (Molecular Dynamics, Sunnyvale, Calif.).

For Western blotting analysis, cell lysates were prepared on ice using 25 mM HEPES buffer, pH7.4, containing 1% NP-40, 150 mM NaCl, 2 mM EDTA, and a protease inhibitor cocktail (Complete™, Boehringer Mannheim). Equal amounts (25 µg/lane) of total cellular proteins were subjected Western blotting with polyclonal rabbit anti-Stra13 (P. Chambon) at 1:2000, followed by incubation with alkaline phosphatase-conjugated anti-rabbit IgG. Protein bands were visualized using ECF substrates (Amersham) on Storm 860 PhosphoImager.

Example VII

Preparation of TAT Fusion Protein

The TAT-N1 fusion protein was prepared from bacteria as described (Vocero-Akbani et al., 2001). The TAT-N1 protein was purified under native conditions using Ni-NTA metal affinity chromatography (Qiagen). After imidazole elution, the TAT-N1 protein was desalted and kept at −80° C. in phosphate-buffered saline containing 15% glycerol until use.

Example VIII

PPARγ2 Promoter Assay

The luciferase reporter construct pX2) under the control of the −603 to +62 PPARγ2 proximal promoter fragment (PPAR) or other deletional subclones was used as described (Tong et al., 2000). NIH-3T3 cells were transiently co-transfected with 0.3 µg each of pXP2 or PPAR and pcDNA3.1His construct expressing a DEC1 fragment using LipofectAmine Plus reagents (Life Technologies). Luciferase activities in cell lysates were measured in triplicates after 40-48 hr of incubation using Monolight 2010 Luminometer (Analytical Luminescence Laboratory, Ann Arbor, Mich.). The luciferase activity is expressed in relation to protein concentrations that vary little from well to well. Alternatively, a *Renilla* luciferase reporter was co-transfected as a control for transfection efficiency.

Example IX

Inhibition of Angiogenesis via PPARγ2

The efficacy of a DEC1 agonist may be assayed as follows. A truncated DEC1 polypeptide having the amino acid sequence of SEQ ID NO:2 may be delivered directly to a mammalian tumor cell in a mammal. DEC1 agonist delivery may consist of a single administration or multiple administrations over a period of time. Corresponding tumor cells to which no polypeptide is delivered (e.g. no injection or buffered saline injection only) may serve as negative controls. The invention contemplates further controls as desired or needed and will be apparent to one of ordinary skill in the art. An additional test group may consist of cells to which the DEC1 agonist is administered in combination with from about 0.1 µM to about 10 µM rosiglitazone. Each group may consist of from about 1 to about 10 or more mammals.

Angiogenesis is preferably monitored before the first administration and periodically thereafter. The effect of each treatment may be assessed by measuring endothelial cell proliferation in particular or more comprehensively as described in O'Reilly et al. 1994. PPARγ2 levels may be monitored according to either Mueller et al., 1998 or Palakurthi et al. 2001.

The results of these experiments, as contemplated by the present example, may show that the DEC1 agonist inhibits angiogenesis in a concentration-dependent manner and that the combined treatment with the DEC1 agonist and rosiglitazone results in a either a more complete inhibition of angiogenesis or inhibition at lower concentrations of one or both agents than when used alone. The effect of the combination therapy may be additive or more than additive.

Example X

Inhibition of Angiogenesis via PPARγ2

The efficiency of a DEC1 agonist may be assayed as follows. A viral or nonviral expression vector comprising a nucleic acid encoding a truncated DEC1 polypeptide having the amino acid sequence of SEQ ID NO:2 may be delivered to a mammalian tumor cell in a mammal. DEC1 agonist expression vector delivery may consist of a single administration or multiple administrations over a period of time. Corresponding tumor cells to which no vector is delivered (e.g. no injection or buffered saline injection only) may serve as negative controls. The invention contemplates further controls as desired or needed and will be apparent to one of ordinary skill in the art. An additional test group may consist of cells to which the DEC1 agonist expression vector is administered in combination with from about 0.1 µM to about 10 µM rosiglitazone. Rosiglitazone may be delivered in a single or multiple administrations. Each group may consist of from about 1 to about 10 or more mammals.

Angiogenesis is preferably monitored before the first administration and periodically thereafter. The effect of each treatment may be assessed by measuring endothelial cell proliferation in particular or more comprehensively as described in O'Reilly et al. 1994. PPARγ2 levels may be monitored according to either Mueller et al., 1998 or Palakurthi et al. 2001. In addition, expression of the DEC1 agonist by the expression vector may be assayed periodically by, for example, Northern or Western blotting techniques well known in the art. See e.g. Example VI.

The results of these experiments, as contemplated by the present example, may show that the DEC1 agonist inhibits angiogenesis in a concentration-dependent manner and that the combined treatment with the DEC1 agonist and rosiglitazone results in a either a more complete inhibition of angiogenesis or inhibition at lower concentrations of one or both agents than when used alone. The effect of the combination therapy may be additive or more than additive.

REFERENCES

The references cited throughout this application and listed below are incorporated herein in their entirety by reference. Citation of these documents is not to be construed as an admission that such documents are available as "prior art" against the instant invention.

Accession No. NM_003670 deposited Mar. 19, 1999
Accession No. NP_003661.1 deposited Mar. 19, 1999
Accession No. NM_011498 deposited Jan. 25, 2000
Accession No. NP_035628.1 deposited Jan. 25, 2000

Alarcon, R., Koumenis, C., Geyer, R. K., Maki, C. G., and Giaccia, A. J. (1999). Hypoxia induces p53 accumulation through MDM2 down-regulation and inhibition of E6-mediated degradation, Cancer Res 59, 6046-51.

Alexander, D. L., Ganem, L. G., Fernandez-Salguero, P., Gonzalez, F., and Jefcoate, C. R. (1998). Aryl-hydrocarbon receptor is an inhibitory regulator of lipid synthesis and of commitment to adipogenesis, J Cell Sci 111, 3311-22.

Armellini, F., Zamboni, M., Robbi, R., Todesco, T., Bissoli, L., Mino, A., Angelini, G., Micciolo, R., and Bosello, O. (1997). The effects of high altitude trekking on body composition and resting metabolic rate, Horm Metab Res 29, 458-61.

Baker, B. W., Boettiger, D., Spooncer, E., and Norton, J. D. (1992). Efficient retroviral-mediated gene transfer into human B lymphoblastoid cells expressing mouse ecotropic viral receptor, Nucleic Acids Res 20, 5234.

Baum, D., and Stern, M. P. (1977). Adipose hypocellularity in cyanotic congenital heart disease, Circulation 55, 916-20.

Berger, J., Moller, D. E. (2002) Mechanism of action of PPARs, Annu. Rev. Med. 53:409-435.

Boudjelal, M., Taneja, R., Matsubara, S., Bouillet, P., Dolle, P., and Chambon, P. (1997). Overexpression of Stra13, a novel retinoic acid-inducible gene of the basic helix-loop-helix family, inhibits mesodermal and promotes neuronal differentiation of P19 cells, Genes Dev 11, 2052-65.

Braissant, O., Foufelle, F., Scotto, C., Dauca, M., and Wahli, W. (1996). Differential expression of peroxisome proliferator-activated receptors (PPARs): tissue distribution of PPAR-a, -b, and -g in the adult rat, Endocrinology 137, 354-66.

Bunn, H. F., and Poyton, R. O. (1996). Oxygen sensing and molecular adaptation to hypoxia, Physiol Rev 76, 839-85.

Caniggia, I., Mostachfi, H., Winter, J., Gassmann, M., Lye, S. J., Kuliszewski, M., and Post, M. (2000). Hypoxia-inducible factor-1 mediates the biological effects of oxygen on human trophoblast differentiation through TGFb3, J Clin Invest 105, 577-87.

Christy, R. J., Kaestner, K. H., Geiman, D. E., and Lane, M. D. (1991). CCAAT/enhancer binding protein gene promoter: binding of nuclear factors during differentiation of 3T3-L1 preadipocytes, Proc Natl Acad Sci USA 88, 2593-7.

Dhar, M., and Taneja, R. (2001). Cross-regulatory interaction between Stra13 and USF results in functional antagonism, Oncogene 20, 4750-6.

Fambrough, D., McClure, K., Kazlauskas, A., and Lander, E. S. (1999). Diverse signaling pathways activated by growth factor receptors induce broadly overlapping, rather than independent, sets of genes, Cell 97, 727-41.

Genbacev, O., Zhou, Y., Ludlow, J. W., and Fisher, S. J. (1997). Regulation of human placental development by oxygen tension, Science 277, 1669-72.

Graeber, T. G., Peterson, J. F., Tsai, M., Monica, K., Fornace, A. J., Jr., and Giaccia, A. J. (1994). Hypoxia induces accumulation of p53 protein, but activation of a G1-phase checkpoint by low-oxygen conditions is independent of p53 status, Mol Cell Biol 14, 6264-77.

Gustafsson, T., and Kraus, W. E. (2001). Exercise-induced angiogenesis-related growth and transcription factors in skeletal muscle, and their modification in muscle pathology, Front Biosci 6, D75-89.

Gustafsson, T., Puntschart, A., Kaijser, L., Jansson, E., and Sundberg, C. J. (1999). Exercise-induced expression of angiogenesis-related transcription and growth factors in human skeletal muscle, Am J Physiol 276, H679-85.

Hu, B., Kim, J. B., Sarraf, P., and Spiegelman, B. M. (1996). Inhibition of adipogenesis through MAP kinase-mediated phosphorylation of PPARg, Science 274, 2100-3.

Hu, E., Tontonoz, P., and Spiegelman, B. M. (1995). Transdifferentiation of myoblasts by the adipogenic transcription factors PPARg and C/EBPa, Proc Natl Acad Sci USA 92, 9856-60.

Imagawa, M., Tsuchiya, T., and Nishihara, T. (1999). Identification of inducible genes at the early stage of adipocyte differentiation of 3T3-L1 cells, Biochem Biophys Res Commun 254, 299-305.

Inoue, K., et al. (2001). Expression of peroxisome proliferator-activated receptor (PPAR)-gamma in human lung cancer, Anticancer Res 21, 2471-2476.

Inuzuka, H., Nanbu-Wakao, R., Masuho, Y., Muramatsu, M., Tojo, H., and Wakao, H. (1999). Differential regulation of immediate early gene expression in preadipocyte cells through multiple signaling pathways, Biochem Biophys Res Commun 265, 664-8.

Ivan, M., Kondo, K., Yang, H., Kim, W., Valiando, J., Ohh, M., Salic, A., Asara, J. M., Lane, W. S., and Kaelin, W. G., Jr. (2001). HIFa targeted for VHL-mediated destruction by proline hydroxylation: implications for $O_2$ sensing, Science 292, 464-8.

Ivanova, A. V., Ivanov, S. V., Danilkovitch-Miagkova, A., and Lerman, M. I. (2001). Regulation of STRA13 by the von Hippel-Lindau tumor suppressor protein, hypoxia, and the UBC9/ubiquitin proteasome degradation pathway, J Biol Chem 276, 15306-15.

Iyer, N. V., Kotch, L. E., Agani, F., Leung, S. W., Laughner, E., Wenger, R. H., Gassmann, M., Gearhart, J. D., Lawler, A. M., Yu, A. Y., and Semenza, G. L. (1998). Cellular and developmental control of $O_2$ homeostasis by hypoxia-inducible factor 1a, Genes Dev 12, 149-62.

Jaakkola, P., Mole, D. R., Tian, Y. M., Wilson, M. I., Gielbert, J., Gaskell, S. J., Kriegsheim, A., Hebestreit, H. F., Mukheiji, M., Schofield, C. J., et al. (2001). Targeting of HIF-a to the von Hippel-Lindau ubiquitylation complex by $O_2$-regulated prolyl hydroxylation, Science 292, 468-72.

Jewell, U. R., Kvietikova, I., Scheid, A., Bauer, C., Wenger, R. H., and Gassmann, M. (2001). Induction of HIF-1a in response to hypoxia is instantaneous, Faseb J 15, 1312-4.

Kageyama, R., and Ohtsuka, T. (1999). The Notch-Hes pathway in mammalian neural development, Cell Res 9, 179-88.

Kallio, P. J., Pongratz, I., Gradin, K., McGuire, J., and Poelinger, L. (1997). Activation of hypoxia-inducible factor 1a: posttranscriptional regulation and conformational change by recruitment of the Arnt transcription factor, Proc Natl Acad Sci USA 94, 5667-72.

Kozak, K. R., Abbott, B., and Hankinson, O. (1997). ARNT-deficient mice and placental differentiation, Dev Biol 191, 297-305.

Lee, S. S., Pineau, T., Drago, J., Lee, E. J., Owens, J. W., Kroetz, D. L., Fernandez-Salguero, P. M., Westphal, H., and Gonzalez, F. J. (1995). Targeted disruption of the a isoform of the peroxisome proliferator-activated receptor gene in mice results in abolishment of the pleiotropic effects of peroxisome proliferators, Mol Cell Biol 15, 3012-22.

Lehmann, J. M., Moore, L. B., Smith-Oliver, T. A., Wilkison, W. O., Willson, T. M., and Kliewer, S. A. (1995). An antidiabetic thiazolidinedione is a high affinity ligand for peroxisome proliferator-activated receptor g (PPARg), J Biol Chem 270, 12953-6.

Lennon, D. P., Edmison, J. M., and Caplan, A. I. (2001). Cultivation of rat marrow-derived mesenchymal stem cells in reduced oxygen tension: effects on in vitro and in vivo osteochondrogenesis, J Cell Physiol 187, 345-55.

Maltepe, E., Schmidt, J. V., Baunoch, D., Bradfield, C. A., and Simon, M. C. (1997). Abnormal angiogenesis and responses to glucose and oxygen deprivation in mice lacking the protein ARNT, Nature 386, 403-7.

Maxwell, P. H., Wiesener, M. S., Chang, G. W., Clifford, S. C., Vaux, E. C., Cockman, M. E., Wykoff, C. C., Pugh, C. W., Maher, E. R., and Ratcliffe, P. J. (1999). The tumour suppressor protein VHL targets hypoxia-inducible factors for oxygen-dependent proteolysis [see comments], Nature 399, 271-5.

Mitchell, J. A., and Yochim, J. M. (1968). Measurement of intrauterine oxygen tension in the rat and its regulation by ovarian steroid hormones, Endocrinology 83, 691-700.

Mortola, J. P., and Naso, L. (1997). Brown adipose tissue and its uncoupling protein in chronically hypoxic rats, Clin Sci (Colch) 93, 349-54.

Mostafa, S. M., Papoutsakis, E. T., and Miller, W. M. (2000). Oxygen tension has significant effects on human megakaryocyte maturation, Exp Hematol 28, 1498.

Mueller, E., Sarraf, P., Tontonoz, P., Evans, R. M., Martin, K. J., Zhang, M., Fletcher, C., Singer, S., Spiegelman, B. M. (1998) Terminal differentiation of human breast cancer through PPAR gamma, Mol Cell. 1(3), 465-470.

Narravula, S., and Colgan, S. P. (2001). Hypoxia-inducible factor 1-mediated inhibition of peroxisome proliferator-activated receptor a expression during hypoxia, J Immunol 166, 7543-8.

Ohh, M., Park, C. W., Ivan, M., Hoffman, M. A., Kim, T. Y., Huang, L. E., Pavletich, N., Chau, V., and Kaelin, W. G. (2000). Ubiquitination of hypoxia-inducible factor requires direct binding to the b-domain of the von Hippel-Lindau protein, Nat Cell Biol 2, 423-7.

O'Reilly, M. S., Holmgren, L., Shing, Y., Chen, C., Rosenthal, R. A., Moses, M., Lane, W. S., Cao, Y., Sage, E. H., Folkman, J. (1994). Angiostatin: a novel angiogenesis inhibitor that mediates the suppression of metastases by a Lewis lung carcinoma, Cell 79, 315-328.

Palakurthi, S. S., Aktas, H., Grubissich, L. M., Mortensen, R. M., Halperin, J. A. (2001) Anticancer effects of thiazolidinediones are independent of peroxisome proliferator-activated receptor gamma and mediated by inhibition of translation initiation, Cancer Res. 61(16), 6213-6218.

Pear, W. S., Nolan, G. P., Scott, M. L., and Baltimore, D. (1993). Production of high-titer helper-free retroviruses by transient transfection, Proc Natl Acad Sci USA 90, 8392-6.

Phillips, M., Enan, E., Liu, P. C., and Matsumura, F. (1995). Inhibition of 3T3-L1 adipose differentiation by 2,3,7,8-tetrachlorodibenzo-p-dioxin, J Cell Sci 108, 395-402.

Probst, M. R., Reisz-Porszasz, S., Agbunag, R. V., Ong, M. S., and Hankinson, O. (1993). Role of the aryl hydrocarbon receptor nuclear translocator protein in aryl hydrocarbon (dioxin) receptor action, Mol Pharmacol 44, 511-8.

Rangwala, S. M., and Lazar, M. A. (2000). Transcriptional control of adipogenesis, Annu Rev Nutr 20, 535-59.

Rodesch, F., Simon, P., Donner, C., and Jauniaux, E. (1992). Oxygen measurements in endometrial and trophoblastic tissues during early pregnancy, Obstet Gynecol 80, 283-5.

Rosen, E. D., and Spiegelman, B. M. (2000). Molecular regulation of adipogenesis, Annu Rev Cell Dev Biol 16, 145-71.

Ross, S. E., Hemati, N., Longo, K. A., Bennett, C. N., Lucas, P. C., Erickson, R. L., and MacDougald, O. A. (2000). Inhibition of adipogenesis by Wnt signaling, Science 289, 950-3.

Ryan, H. E., Lo, J., and Johnson, R. S. (1998). HIF-1a is required for solid tumor formation and embryonic vascularization, Embo J 17, 3005-15.

Ryan, H. E., Poloni, M., McNulty, W., Elson, D., Gassmann, M., Arbeit, J. M., and Johnson, R. S. (2000). Hypoxia-inducible factor-1a is a positive factor in solid tumor growth, Cancer Res 60, 4010-5.

Schwarz, E. J., Reginato, M. J., Shao, D., Krakow, S. L., and Lazar, M. A. (1997). Retinoic acid blocks adipogenesis by inhibiting C/EBPb-mediated transcription, Mol Cell Biol 17, 1552-61.

Schwarze, S. R., and Dowdy, S. F. (2000). In vivo protein transduction: intracellular delivery of biologically active proteins, compounds and DNA, Trends Pharmacol Sci 21, 45-8.

Seagroves, T. N., Ryan, H. E., Lu, H., Wouters, B. G., Knapp, M., Thibault, P., Laderoute, K., and Johnson, R. S. (2001). Transcription factor HIF-1 is a necessary mediator of the pasteur effect in mammalian cells, Mol Cell Biol 21, 3436-44.

Selvarajan, S., Lund, L. R., Takeuchi, T., Craik, C. S., and Werb, Z. (2001). A plasma kallikrein-dependent plasminogen cascade required for adipocyte differentiation, Nat Cell Biol 3, 267-75.

Semenza, G. L. (1999). Regulation of mammalian $O_2$ homeostasis by hypoxia-inducible factor 1, Annu Rev Cell Dev Biol 15, 551-78.

Semenza, G. L., and Wang, G. L. (1992). A nuclear factor induced by hypoxia via de novo protein synthesis binds to the human erythropoietin gene enhancer at a site required for transcriptional activation, Mol Cell Biol 12, 5447-54.

Shen, M., Kawamoto, T., Yan, W., Nakamasu, K., Tamagami, M., Koyano, Y., Noshiro, M., and Kato, Y. (1997). Molecular characterization of the novel basic helix-loop-helix protein DEC1 expressed in differentiated human embryo chondrocytes, Biochem Biophys Res Commun 236, 294-8.

Staal, F. J., Weerkamp, F., Langerak, A. W., Hendriks, R. W., and Clevers, H. C. (2001). Transcriptional control of T lymphocyte differentiation, Stem Cells 19, 165-79.

Studer, L., Csete, M., Lee, S. H., Kabbani, N., Walikonis, J., Wold, B., and McKay, R. (2000). Enhanced proliferation, survival, and dopaminergic differentiation of CNS precursors in lowered oxygen, J Neurosci 20, 7377-83.

Tanaka, M., Mizuta, K., Koba, F., Ohira, Y., Kobayashi, T., and Honda, Y. (1997). Effects of exposure to hypobarichypoxia on body weight, muscular and hematological characteristics, and work performance in rats, Jpn J Physiol 47, 51-7.

Tong, Q., Dalgin, G., Xu, H., Ting, C. N., Leiden, J. M., and Hotamisligil, G. S. (2000). Function of GATA transcription factors in preadipocyte-adipocyte transition, Science 290, 134-8.

Tontonoz, P., Hu, E., Devine, J., Beale, E. G., and Spiegelman, B. M. (1995). PPARg2 regulates adipose expression of the phosphoenolpyruvate carboxykinase gene, Mol Cell Biol 15, 351-7.

Tontonoz, P., Hu, E., Graves, R. A., Budavari, A. I., and Spiegelman, B. M. (1994). nPPARg2: tissue-specific regulator of an adipocyte enhancer, Genes Dev 8, 1224-34.

Van Etten, L. M., Verstappen, F. T., and Westerterp, K. R. (1994). Effect of body build on weight-training-induced adaptations in body composition and muscular strength, Med Sci Sports Exerc 26, 515-21.

Vocero-Akbani, A., Chellaiah, M. A., Hruska, K. A., and Dowdy, S. F. (2001). Protein transduction: delivery of Tat-GTPase fusion proteins into mammalian cells, Methods Enzymol 332, 36-49.

Wang, G. L., Jiang, B. H., Rue, E. A., and Semenza, G. L. (1995a). Hypoxia-inducible factor 1 is a basic-helix-loop-helix-PAS heterodimer regulated by cellular $O_2$ tension, Proc Natl Acad Sci USA 92, 5510-4.

Wang, N. D., Finegold, M. J., Bradley, A., Ou, C. N., Abdelsayed, S. V., Wilde, M. D., Taylor, L. R., Wilson, D. R., and Darlington, G. J. (1995b). Impaired energy homeostasis in C/EBPa knockout mice, Science 269, 1108-12.

Westerterp, K. R., Kayser, B., Wouters, L., Le Trong, J. L., and Richalet, J. P. (1994a). Energy balance at high altitude of 6,542 m, J Appl Physiol 77, 862-6.

Westerterp, K. R., Meijer, G. A., Schoffelen, P., and Janssen, E. M. (1994b). Body mass, body composition and sleeping metabolic rate before, during and after endurance training, Eur J Appl Physiol Occup Physiol 69, 203-8.

Wu, Z., Bucher, N. L., and Farmer, S. R. (1996). Induction of peroxisome proliferator-activated receptor g during the conversion of 3T3 fibroblasts into adipocytes is mediated by C/EBPb, C/EBPd, and glucocorticoids, Mol Cell Biol 16, 4128-36.

Wu, Z., Xie, Y., Bucher, N. L., and Farmer, S. R. (1995). Conditional ectopic expression of C/EBPb in NIH-3T3 cells induces PPARg and stimulates adipogenesis, Genes Dev 9, 2350-63.

Wu, Z., Xie, Y., Morrison, R. F., Bucher, N. L., and Farmer, S. R. (1998). PPARg induces the insulin-dependent glucose transporter GLUT4 in the absence of C/EBPa during the conversion of 3T3 fibroblasts into adipocytes, J Clin Invest 101, 22-32.

Yeh, W. C., Cao, Z., Classon, M., and McKnight, S. L. (1995). Cascade regulation of terminal adipocyte differentiation by three members of the C/EBP family of leucine zipper proteins, Genes Dev 9, 168-81.

Yu, A. Y., Shimoda, L. A., Iyer, N. V., Huso, D. L., Sun, X., McWilliams, R., Beaty, T., Sham, J. S., Wiener, C. M., Sylvester, J. T., and Semenza, G. L. (1999). Impaired physiological responses to chronic hypoxia in mice partially deficient for hypoxia-inducible factor 1a, J Clin Invest 103, 691-6.

SEQUENCE LISTING

```
<160> NUMBER OF SEQ ID NOS: 7

<210> SEQ ID NO 1
<211> LENGTH: 2922
<212> TYPE: DNA
<213> ORGANISM: Human
<220> FEATURE:
<221> NAME/KEY: gene
<222> LOCATION: (1)...(2922)
<223> OTHER INFORMATION: BHLHB2 (DEC1)
<220> FEATURE:
<221> NAME/KEY: variation
<222> LOCATION: (27)...(27)
<223> OTHER INFORMATION: C or T
<220> FEATURE:
<221> NAME/KEY: variation
<222> LOCATION: (196)...(196)
<223> OTHER INFORMATION: C or T
<220> FEATURE:
<221> NAME/KEY: CDS
<222> LOCATION: (197)...(145)
<223> OTHER INFORMATION: BHLHB2
<220> FEATURE:
<221> NAME/KEY: variation
<222> LOCATION: (829)...(829)
<223> OTHER INFORMATION: C or T
<220> FEATURE:
<221> NAME/KEY: variation
<222> LOCATION: (2504)...(2504)
<223> OTHER INFORMATION: A or T
<220> FEATURE:
<221> NAME/KEY: variation
<222> LOCATION: (2732)...(2732)
<223> OTHER INFORMATION: A or C
<220> FEATURE:
<221> NAME/KEY: variation
```

```
<222> LOCATION: (2770)...(2770)
<223> OTHER INFORMATION: A or G
<220> FEATURE:
<221> NAME/KEY: variation
<222> LOCATION: (2891)...(2891)
<223> OTHER INFORMATION: A or T
<220> FEATURE:
<221> NAME/KEY: polyA_signal
<222> LOCATION: (2896)...(2901)
<220> FEATURE:
<221> NAME/KEY: polyA_site
<222> LOCATION: (2922)...(2922)
<308> DATABASE ACCESSION NUMBER: NM_003670
<309> DATABASE ENTRY DATE: 1999-03-19

<400> SEQUENCE: 1
ggacaccggg ccatgcacgc ccccaactga agctgcatct caaagccgaa gattccagca      60
gcccagggga tttcaaagag ctcagactca gaggaacatc tgcggagaga cccccgaagc     120
cctctccagg gcagtcctca tccagacgct ccgctagtgc agacaggagc gcgcagtggc     180
cccggctcgc cgcgccatgg agcggatccc cagcgcgcaa ccacccccg cctgcctgcc      240
caaagcaccg ggactggagc acggagacct accaggatg tacctgccc acatgtacca      300
agtgtacaag tcaagacggg aataaagcg agcgaggac agcaaggaga cctacaaatt       360
gccgcaccgg ctcatcgaga aaagagacg tgaccggatt aacgagtgca tcgcccagct     420
gaaggatctc ctacccgaac atctcaaact acaactttg ggtcacttgg aaaaagcagt     480
ggttcttgaa cttaccttga agcatgtgaa agcactaaca aacctaattg atcagcagca     540
gcagaaaatc attgccctgc agagtggttt acaagctggt gagctgtcag ggagaaatgt     600
cgaaacaggt caagagatgt tctgctcagg tttccagaca tgtgcccggg aggtgcttca     660
gtatctggcc aagcacgaga acactcggga cctgaagtct tcgcagcttg tcacccacct     720
ccaccgggtg gtctcggagc tgctgcaggg tggtacctcc aggaagccat cagacccagc     780
tcccaaagtg atggacttca aggaaaaacc cagctctccg gccaaaggtt cggaaggtcc     840
tgggaaaaac tgcgtgccag tcatccagcg gactttcgct cactcgagtg gggagcagag     900
cggcagcgac acgacacag acagtggcta tggaggagaa tcggagaagg gcgacttgcg      960
cagtgagcag ccgtgcttca aaagtgacca cggacgcagg ttcacgatgg agaaaggat    1020
cggcgcaatt aagcaagagt ccgaagaacc ccccacaaaa aagaaccgga tgcagctttc    1080
ggatgatgaa ggccatttca ctagcagtga cctgatcagc tccccgttcc tgggcccaca    1140
cccacaccag cctcctttct gcctgccctt tacctgatc ccaccttcag cgactgccta    1200
cctgcccatg ctggagaagt gctggtatcc cacctcagtg ccagtgctat acccaggcct    1260
caacgcctct gccgcagccc tctctagctt catgaaccca gacaagatct cggctccctt    1320
gctcatgccc cagagactcc cttctccctt gccagctcat ccgtccgtcg actcttctgt    1380
cttgctccaa gctctgaagc caatcccccc tttaaactta gaaaccaaag actaaactct    1440
ctaggggatc ctgctgcttt gctttccttc ctcgctactt cctaaaaagc aacaaaaaag    1500
tttttgtgaa tgctgcaaga ttgttgcatt gtgtatactg agataatctg aggcatggag    1560
agcagattca gggtgtgtgt gtgtgtgtgt gtgtgtgtgt gtatgtgcgt gtgcgtgcac    1620
atgtgtgcct gcgtgttggt ataggacttt aaagctcctt ttggcatagg gaagtcacga    1680
aggattgctt gacatcagga gacttggggg ggattgtagc agacgtctgg gcttttcccc    1740
acccagagaa tagccccctt cgatacacat cagctggatt ttcaaaagct tcaaagtctt    1800
ggtctgtgag tcactcttca gtttgggagc tgggtctgtg gctttgatca gaaggtactt    1860
```

-continued

```
tcaaaagagg gctttccagg gctcagctcc caaccagctg ttaggacccc acccttttgc      1920
ctttattgtc gacgtgactc accagacgtc ggggagagag agcagtcaga ccgagctttc      1980
tgctaacatg gggaggtagc aggcactggc atagcacggt agtggtttgg ggaggtttcc      2040
gcaggtctgc tccccacccc tgcctcggaa gaataaagag aatgtagttc cctactcagg      2100
ctttcgtagt gattagctta ctaaggaact gaaaatgggc cccttgtaca agctgagctg      2160
ccccggaggg agggaggagt tccctgggct tctggcacct gtttctaggc ctaaccatta      2220
gtacttactg tgcagggaac caaaccaagg tctgagaaat gcggacaccc cgagcgagca      2280
ccccaaagtg cacaaagctg agtaaaaagc tgccccttc aaacagaact agactcagtt       2340
ttcaattcca tcctaaaact cctttttaacc aagcttagct tctcaaaggc ctaaccaagc     2400
cttggcaccg ccagatcctt tctgtaggct aattcctctt gcccaacggc atatggagtg      2460
tccttattgc taaaaaggat tccgtctcct tcaaagaagt tttattttg gtccagagta       2520 cttgttttcc cgatgtgtcc agccagctcc gcagcagctt ttcaagatgc actatgcctg     2580
attgctgatc gtgttttaac ttttttcttt cctgttttta ttttggtatt aagtcgttgc      2640
ctttatttgt aaagctgtta taaatatata ttatataaat atattaaaaa ggaaaatgtt     2700
tcagatgttt atttgtataa ttacttgatt cacacagtga gaaaaaatga atgtattcct     2760 gttttttgaag agaagaataa ttttttttttc tctagggaga ggtacagtgt ttatattttg  2820
gagccttcct gaaggtgtaa aattgtaaat attttttatct atgagtaaat gttaagtagt   2880
tgttttaaaa tacttaataa aataattctt ttcctgtgga ag                       2922
```

<210> SEQ ID NO 2
<211> LENGTH: 412
<212> TYPE: PRT
<213> ORGANISM: Human
<308> DATABASE ACCESSION NUMBER: NP_003661.1
<309> DATABASE ENTRY DATE: 1999-03-19

<400> SEQUENCE: 2

```
Met Glu Arg Ile Pro Ser Ala Gln Pro Pro Ala Cys Leu Pro Lys
 1               5                  10                  15

Ala Pro Gly Leu Glu His Gly Asp Leu Pro Gly Met Tyr Pro Ala His
                20                  25                  30

Met Tyr Gln Val Tyr Lys Ser Arg Arg Gly Ile Lys Arg Ser Glu Asp
            35                  40                  45

Ser Lys Glu Thr Tyr Lys Leu Pro His Arg Leu Ile Glu Lys Lys Arg
    50                  55                  60

Arg Asp Arg Ile Asn Glu Cys Ile Ala Gln Leu Lys Asp Leu Leu Pro
65                  70                  75                  80

Glu His Leu Lys Leu Thr Thr Leu Gly His Leu Glu Lys Ala Val Val
                85                  90                  95

Leu Glu Leu Thr Leu Lys His Val Lys Ala Leu Thr Asn Leu Ile Asp
            100                 105                 110

Gln Gln Gln Gln Lys Ile Ile Ala Leu Gln Ser Gly Leu Gln Ala Gly
        115                 120                 125

Glu Leu Ser Gly Arg Asn Val Glu Thr Gly Gln Glu Met Phe Cys Ser
    130                 135                 140

Gly Phe Gln Thr Cys Ala Arg Glu Val Leu Gln Tyr Leu Ala Lys His
145                 150                 155                 160

Glu Asn Thr Arg Asp Leu Lys Ser Ser Gln Leu Val Thr His Leu His
                165                 170                 175
```

-continued

```
Arg Val Val Ser Glu Leu Leu Gln Gly Gly Thr Ser Arg Lys Pro Ser
            180                 185                 190

Asp Pro Ala Pro Lys Val Met Asp Phe Lys Glu Lys Pro Ser Ser Pro
        195                 200                 205

Ala Lys Gly Ser Glu Gly Pro Gly Lys Asn Cys Val Pro Val Ile Gln
    210                 215                 220

Arg Thr Phe Ala His Ser Ser Gly Glu Gln Ser Gly Ser Asp Thr Asp
225                 230                 235                 240

Thr Asp Ser Gly Tyr Gly Gly Glu Ser Glu Lys Gly Asp Leu Arg Ser
                245                 250                 255

Glu Gln Pro Cys Phe Lys Ser Asp His Gly Arg Arg Phe Thr Met Gly
            260                 265                 270

Glu Arg Ile Gly Ala Ile Lys Gln Glu Ser Glu Glu Pro Pro Thr Lys
        275                 280                 285

Lys Asn Arg Met Gln Leu Ser Asp Asp Glu Gly His Phe Thr Ser Ser
    290                 295                 300

Asp Leu Ile Ser Ser Pro Phe Leu Gly Pro His Pro His Gln Pro Pro
305                 310                 315                 320

Phe Cys Leu Pro Phe Tyr Leu Ile Pro Pro Ser Ala Thr Ala Tyr Leu
                325                 330                 335

Pro Met Leu Glu Lys Cys Trp Tyr Pro Thr Ser Val Pro Val Leu Tyr
            340                 345                 350

Pro Gly Leu Asn Ala Ser Ala Ala Ala Leu Ser Ser Phe Met Asn Pro
        355                 360                 365

Asp Lys Ile Ser Ala Pro Leu Leu Met Pro Gln Arg Leu Pro Ser Pro
    370                 375                 380

Leu Pro Ala His Pro Ser Val Asp Ser Ser Val Leu Leu Gln Ala Leu
385                 390                 395                 400

Lys Pro Ile Pro Pro Leu Asn Leu Glu Thr Lys Asp
                405                 410

<210> SEQ ID NO 3
<211> LENGTH: 2909
<212> TYPE: DNA
<213> ORGANISM: Mus musculus
<220> FEATURE:
<221> NAME/KEY: gene
<222> LOCATION: (1)...(2909)
<223> OTHER INFORMATION: BHLHB2 (Stra13;CR8)
<220> FEATURE:
<221> NAME/KEY: CDS
<222> LOCATION: (217)...(1452)
<223> OTHER INFORMATION: BHLHB2 (eip1; E47 interaction protein)
<308> DATABASE ACCESSION NUMBER: NM_011498
<309> DATABASE ENTRY DATE: 2000-01-25

<400> SEQUENCE: 3
gccagaagcc gtggggacac ccggccatgc acgcccccaa ctgaagcgac acctcaaagc      60
cgctgctcct ggcatcccag cgcattgcaa ggaagctcag gctagctcat aggaacatac     120
ctcttgagac cctcggatcc tcccttccag ggcagccctt tctcagactc tactaagtgc     180
agacaggagc gcacagtggc ccctgctcgc cgcatcatgg aacggatccc cagcgcgcaa     240
ccacctccta cctgcctgcc caaagctcca gggctggagc acggagacct gtcagggatg     300 gatttttgccc acatgtacca agtgtacaag tccaggcggg gaataaaacg gagcgaagac     360
agcaaggaaa cttacaaaact gccgcaccgg ctgattgaga aaagagacg tgaccggatt     420 aacgagtgca ttgcccagct gaaggatctc ctacccgaac atctcaaact tactactttg     480
```

```
ggtcacttgg aaaaagcagt ggttctggag cttacgttga agcacgtgaa agcattgaca    540
aatctaattg atcagcagca gcagaaaatc attgccctgc agagcggttt acaagctggt    600
gatttgtcgg gaagaaatct cgaggcaggg caagaaatgt tctgctcagg tttccagact    660
tgtgcccgtg aggtacttca gtacctggcg aagcatgaga cactcggga cctgaaatct     720 tcccagctcg tcactcatct ccatcgtgtg gtctcggagc tgctgcaggg tggtgcttcc    780
aggaaaccat tggactcggc tcccaaagcc gtggacttga agagaagcc cagcttccta     840 gccaagggat cagaaggccc agggaaaaac tgtgtgccag tcatccagcg acttttgct     900 ccctcgggtg gggagcagag cggcagtgac acggacacag acagtggcta tggaggtgaa    960
ttggagaaag gggacttgcg cagtgaacag ccgtacttca aaagcgacca tggacgcagg   1020
ttcgccgtgg agaacgtgt cagcacaatt aagcaagaat ccgaagagcc ccccaccaaa    1080
aagagccgaa tgcagctctc agaagaggaa ggccacttcg cgggcagtga tctgatgggt   1140
tccccatttc ttgggccaca cccacatcag cctcctttt gccttccctt ctatctcatc    1200
ccaccatcgg ccactgccta cctgcctatg ctggagaaat gctggtaccc cacctctgtg   1260
ccagtgttat acccaggcct caacacctca gctgcagccc tctccagctt catgaaccca   1320
gacaagatac cgactcccctt gcttctgccc cagagactcc cttctccttt ggcacattcg   1380
tcccttgact cttcggcctt gctccaggct ttgaagcaga tccctccttt aaacttagaa    1440
accaaagact aaactctgga gggatctcct gctgccttgc tttcttttcct ccctaattcc   1500 aaaaaccacg aaggtttccc tgagtgcaga gagatcagcc caccctgcag acccacagag   1560
aagattcaga gtgtgtgtga gagtgagtga gtgtgcgtgc gtgcgtgctt gtatgtatgt    1620
ttgtatatgt aggacaataa gttccttctg acacaaggga gacacgagaa ggatagcctg   1680
acatcagatg acagactgga ggactgtagc acatctctgg gcgtttccct acccagagaa   1740
gagccccccc ccccttttgat acaaatcggt tggattttca tatgcttcaa aggcttgatc    1800
tgtgagtcac tctccagttt gggacatggg tctgtctgtg gctttgagaa aaggtacttt   1860
caaaagaggg ctttccagag cacagctcac agccagctgt taggaccca cccttctccc     1920 tttattgtgg aggtgactca cagcagactg acagtggtca ggctgagctt tctgctaagg   1980
tggtgaggtc gccaacactg gcatgtctcg gtagtggttt gggcaaattt ctgcaggtcc   2040
cttcccccca accccgtctc tgatgaataa agaccatgag tggagttcct taactcaggc   2100
ttttgtgagt agtttactaa ggaactgaaa atggtcccct ttgtccaagc tgagctgcta   2160
gggaatcaag gtgaactgga cccgtcctca ggcctctggc acctgtttct agctctcact   2220
tctacggcat gctgtccaag gaaccaaagg aggctctcgg agatgccccc aaacgtccca   2280
aagtacacag agctaagtaa tcaattgcta cacttattgc acagctagac acggatttca   2340
agtgtatcct aaagctttga accaagctta gcttctcaaa ggcctagcag agctttggca   2400
ccccaagatc ctttctgtag ctatttcct cttgcccagc agcggatgga gcgtccttgc    2460
taaaaagggt tccatctcct ttaaggacgt tttattttg atccagagtc cttgtttcct    2520
tgacttgctc caccagccct gcaccagctt tccaaatgca ctctgcttgt gttgaaattc   2580
tcccattttt atttgggcat aaaagttgtt gcctttattt gtaaagctgt tataaatata   2640
tattatataa atatatgaca aaggaaaatg tttcagatgt ctatttgtat aattacttga   2700
tctacacagt gaggaaaaaa atgaatgtat ttctgttttt gaagagaata atttttttct   2760
ctagggagag gcgaggttac agtgtttata ttttggaacc ttcctgaagg tgtgaaattg   2820
taaatatttt tatctaagta aatgttaagc agttgtttta aaaatactta ataaaataag   2880
```
cttttttcct gtggaagcga cagtatcgg                                             2909

<210> SEQ ID NO 4
<211> LENGTH: 411
<212> TYPE: PRT
<213> ORGANISM: Mus musculus
<308> DATABASE ACCESSION NUMBER: NP_035628.1
<309> DATABASE ENTRY DATE: 2000-01-25

<400> SEQUENCE: 4

```
Met Glu Arg Ile Pro Ser Ala Gln Pro Pro Thr Cys Leu Pro Lys
 1               5                  10                  15

Ala Pro Gly Leu Glu His Gly Asp Leu Ser Gly Met Asp Phe Ala His
             20                  25                  30

Met Tyr Gln Val Tyr Lys Ser Arg Arg Gly Ile Lys Arg Ser Glu Asp
         35                  40                  45

Ser Lys Glu Thr Tyr Lys Leu Pro His Arg Leu Ile Glu Lys Lys Arg
 50                  55                  60

Arg Asp Arg Ile Asn Glu Cys Ile Ala Gln Leu Lys Asp Leu Leu Pro
 65                  70                  75                  80

Glu His Leu Lys Leu Thr Thr Leu Gly His Leu Glu Lys Ala Val Val
                 85                  90                  95

Leu Glu Leu Thr Leu Lys His Val Lys Ala Leu Thr Asn Leu Ile Asp
            100                 105                 110

Gln Gln Gln Gln Lys Ile Ile Ala Leu Gln Ser Gly Leu Gln Ala Gly
            115                 120                 125

Asp Leu Ser Gly Arg Asn Leu Glu Ala Gly Gln Glu Met Phe Cys Ser
    130                 135                 140

Gly Phe Gln Thr Cys Ala Arg Glu Val Leu Gln Tyr Leu Ala Lys His
145                 150                 155                 160

Glu Asn Thr Arg Asp Leu Lys Ser Ser Gln Leu Val Thr His Leu His
                165                 170                 175

Arg Val Val Ser Glu Leu Leu Gln Gly Gly Ala Ser Arg Lys Pro Leu
            180                 185                 190

Asp Ser Ala Pro Lys Ala Val Asp Leu Lys Glu Lys Pro Ser Phe Leu
        195                 200                 205

Ala Lys Gly Ser Glu Gly Pro Gly Lys Asn Cys Val Pro Val Ile Gln
    210                 215                 220

Arg Thr Phe Ala Pro Ser Gly Gly Glu Gln Ser Gly Ser Asp Thr Asp
225                 230                 235                 240

Thr Asp Ser Gly Tyr Gly Gly Glu Leu Glu Lys Gly Asp Leu Arg Ser
                245                 250                 255

Glu Gln Pro Tyr Phe Lys Ser Asp His Gly Arg Arg Phe Ala Val Gly
            260                 265                 270

Glu Arg Val Ser Thr Ile Lys Gln Glu Ser Glu Glu Pro Pro Thr Lys
        275                 280                 285

Lys Ser Arg Met Gln Leu Ser Glu Glu Glu Gly His Phe Ala Gly Ser
    290                 295                 300

Asp Leu Met Gly Ser Pro Phe Leu Gly Pro His Pro His Gln Pro Pro
305                 310                 315                 320

Phe Cys Leu Pro Phe Tyr Leu Ile Pro Pro Ser Ala Thr Ala Tyr Leu
                325                 330                 335

Pro Met Leu Glu Lys Cys Trp Tyr Pro Thr Ser Val Pro Val Leu Tyr
            340                 345                 350
```

```
Pro Gly Leu Asn Thr Ser Ala Ala Leu Ser Ser Phe Met Asn Pro
        355                 360                 365

Asp Lys Ile Pro Thr Pro Leu Leu Leu Pro Gln Arg Leu Pro Ser Pro
    370                 375                 380

Leu Ala His Ser Ser Leu Asp Ser Ser Ala Leu Leu Gln Ala Leu Lys
385                 390                 395                 400

Gln Ile Pro Pro Leu Asn Leu Glu Thr Lys Asp
                405                 410

<210> SEQ ID NO 5
<211> LENGTH: 14
<212> TYPE: DNA
<213> ORGANISM: Artificial Sequence
<220> FEATURE:
<223> OTHER INFORMATION: C/EBPbeta site

<400> SEQUENCE: 5
caatgtagca acgt                                             14

<210> SEQ ID NO 6
<211> LENGTH: 14
<212> TYPE: DNA
<213> ORGANISM: Artificial Sequence
<220> FEATURE:
<223> OTHER INFORMATION: C/EBPalpha site

<400> SEQUENCE: 6
gtcttgccaa agca                                             14

<210> SEQ ID NO 7
<211> LENGTH: 11
<212> TYPE: PRT
<213> ORGANISM: Artificial Sequence
<220> FEATURE:
<223> OTHER INFORMATION: Protein transduction domain derived from Human
      Immunodeficiency Virus

<400> SEQUENCE: 7

Tyr Gly Arg Lys lys Arg Arg Gln Arg Arg Arg
1               5                   10
```

We claim:

1. A method of inhibiting adipogenesis comprising: contacting at least one cell with a truncated DEC1/Stra13 polypeptide lacking a DEC1/Stra13 repressor domain, wherein the truncated DEC1/Stra13 polypeptide comprises a basic helix loop helix domain of DEC1/Stra13, in an amount effective to decrease PPARγ2 promoter activity, whereby expression of PPARγ2 is reduced and said adipogenesis is inhibited.

2. The method of claim 1, wherein the truncated polypeptide has the amino acid sequence of amino acids 1-141 of SEQ ID NO:2.

3. The method of claim 1, wherein the truncated polypeptide has the amino acid sequence of amino acids 1-141 of SEQ ID NO:4.

4. The method of claim 1, wherein the truncated polypeptide further comprises a peptide having the amino acid sequence of SEQ ID NO:7.

5. The method of claim 2, wherein the truncated polypeptide further comprises a peptide having the amino acid sequence of SEQ ID NO:7.

6. The method of claim 3, wherein the truncated polypeptide further comprises a peptide having the amino acid sequence of SEQ ID NO:7.

7. The method of claim 1, wherein said at least one cell is a mammalian cell.

8. The method of claim 1, wherein said at least one cell as a 3T3-L1 cell.

9. A method of inhibiting adipogenesis comprising: contacting at least one cell with a full length DEC1/Stra13 polypeptide; in an amount effective to decrease PPARγ2 promoter activity, whereby expression of PPARγ2 is reduced and said adipogenesis is inhibited.

10. The method of claim 9, wherein said at least one cell is a mammalian cell.

11. The method of claim 9, wherein said at least one cell as a 3T3-L1 cell.

* * * * *